(12) United States Patent
Ronacher et al.

(10) Patent No.: US 7,927,546 B2
(45) Date of Patent: Apr. 19, 2011

(54) DEVICE FOR THE ANALYSIS OF LIQUID SAMPLES

(75) Inventors: Bernhard Ronacher, Linz (AT); Christoph Reschreiter, Linz (AT)

(73) Assignee: Anagnostics Bioanalysis GmbH, Linz (AT)

( * ) Notice: Subject to any disclaimer, the term of this patent is extended or adjusted under 35 U.S.C. 154(b) by 388 days.

(21) Appl. No.: 12/089,358

(22) PCT Filed: Oct. 9, 2006

(86) PCT No.: PCT/AT2006/000411
§ 371 (c)(1),
(2), (4) Date: Apr. 4, 2008

(87) PCT Pub. No.: WO2007/041734
PCT Pub. Date: Apr. 19, 2007

(65) Prior Publication Data
US 2008/0233590 A1    Sep. 25, 2008

(30) Foreign Application Priority Data
Oct. 7, 2005 (AT) ............................... A 1641/2005

(51) Int. Cl.
*G01N 9/30* (2006.01)
*B04B 3/00* (2006.01)
*C12Q 1/68* (2006.01)
*B04B 15/00* (2006.01)
*B04B 9/14* (2006.01)

(52) U.S. Cl. ........... 422/72; 422/102; 435/287.1; 435/6; 494/10; 73/1.87

(58) Field of Classification Search .................. 73/1.87
See application file for complete search history.

(56) References Cited

U.S. PATENT DOCUMENTS

| 4,580,897 | A | * | 4/1986 | Nelson et al. ................. 356/246 |
| 5,173,748 | A | | 12/1992 | Bilhorn ......................... 356/328 |
| 5,585,639 | A | | 12/1996 | Dorsel et al. ................ 250/458.1 |
| 5,641,658 | A | | 6/1997 | Adams et al. ................. 435/91.2 |
| 5,961,799 | A | | 10/1999 | Matsumoto et al. .......... 204/400 |
| 5,993,741 | A | * | 11/1999 | Behnk ............................. 422/64 |
| 6,635,470 | B1 | * | 10/2003 | Vann ............................... 506/16 |
| 6,844,158 | B1 | | 1/2005 | Mitsuhashi ....................... 435/6 |

(Continued)

FOREIGN PATENT DOCUMENTS
DE    198 28 837    4/1999
(Continued)

OTHER PUBLICATIONS
Austrian Search Report and Written Opinion, issued in Austrian Application No. PCT/AT2006/000411, dated Oct. 9, 2006.
(Continued)

*Primary Examiner* — In Suk Bullock
*Assistant Examiner* — Jennifer Wecker
(74) *Attorney, Agent, or Firm* — Fulbright & Jaworski

(57) ABSTRACT

The present invention relates to devices for the analysis of liquid samples, comprising a rotational-symmetric rotor (1) which is insertable into a sample container (11), wherein an annular gap (32) is provided between the sample container (11) and the rotor (1), and the rotor (1) has at least one flow channel (7) for transporting liquids and/or gases into and/or from the interior of the sample container (11), wherein on the rotor (1) and, optionally, on the sample container (11), means for centred mounting of the rotor (1) are provided.

52 Claims, 22 Drawing Sheets

Section A-A

U.S. PATENT DOCUMENTS

| | | | |
|---|---|---|---|
| 7,258,837 B2 | 8/2007 | Yager et al. | 422/57 |
| 7,666,357 B2 * | 2/2010 | Sattler et al. | 422/99 |
| 2002/0155591 A1 * | 10/2002 | Farina et al. | 435/288.5 |
| 2002/0177144 A1 | 11/2002 | Remacle et al. | 435/6 |
| 2003/0049866 A1 | 3/2003 | Bushway et al. | 436/518 |
| 2003/0124623 A1 | 7/2003 | Yager et al. | 506/9 |
| 2004/0053327 A1 | 3/2004 | Muller | 435/7.1 |
| 2004/0096991 A1 | 5/2004 | Zhang | 436/518 |
| 2004/0224419 A1 * | 11/2004 | Zheng et al. | 436/69 |
| 2005/0255578 A1 * | 11/2005 | Ronacher | 435/287.1 |
| 2007/0156006 A1 * | 7/2007 | Smith et al. | 600/16 |
| 2007/0264705 A1 * | 11/2007 | Dodgson | 435/283.1 |
| 2008/0107568 A1 * | 5/2008 | Murashige et al. | 422/72 |
| 2008/0166705 A1 * | 7/2008 | Schwoebel et al. | 435/6 |

FOREIGN PATENT DOCUMENTS

| | | |
|---|---|---|
| DE | 199 39 252 | 4/2001 |
| DE | 101 60 983 | 6/2003 |
| EP | 0 011 798 | 6/1980 |
| EP | 0 370 694 | 5/1990 |
| EP | 0 947 819 | 10/1999 |
| EP | 0 947 824 | 10/1999 |
| EP | 1 186 699 | 3/2002 |
| JP | 2001 299 346 | 10/2001 |
| WO | WO 90/06042 | 6/1990 |
| WO | WO 93/09250 | 5/1993 |
| WO | WO 94/09156 | 4/1994 |
| WO | WO 97/12030 | 4/1997 |
| WO | WO 98/44152 | 10/1998 |
| WO | WO 00/12759 | 3/2000 |
| WO | WO 00/25113 | 5/2000 |
| WO | WO 00/40334 | 7/2000 |
| WO | WO 00/62549 | 10/2000 |
| WO | WO 00/79326 | 12/2000 |
| WO | WO 01/25759 | 4/2001 |
| WO | WO 01/53822 | 7/2001 |
| WO | WO 01/84644 | 11/2001 |
| WO | WO 02/08457 | 1/2002 |
| WO | WO 03/014400 | 2/2003 |
| WO | WO 03/015189 | 2/2003 |
| WO | WO 03/100401 | 12/2003 |

OTHER PUBLICATIONS

Office Action, issued in U.S. Appl. No. 10/516,049, mailed Sep. 12, 2005.
Response to Office Action, filed in U.S. Appl. No. 10/516,049, submitted Dec. 12, 2005.
Office Action, issued in U.S. Appl. No. 10/516,049, mailed Feb. 28, 2006.
Response to Office Action, filed in U.S. Appl. No. 10/516,049, submitted Apr. 12, 2006.
Office Action, issued in U.S. Appl. No. 10/516,049, mailed May 4, 2006.
Response to Office Action, filed in U.S. Appl. No. 10/516,049, submitted Jun. 23, 2006.
Office Action, issued in U.S. Appl. No. 10/516,049, mailed Sep. 11, 2006.
Response to Office Action, filed in U.S. Appl. No. 10/516,049, submitted Dec. 11, 2006.
Office Action, issued in U.S. Appl. No. 10/516,049, mailed Mar. 5, 2007.
Appeal Brief, filed in U.S. Appl. No. 10/516,049, filed Aug. 6, 2007.
Examiner's Answer to Appeal Brief, U.S. Appl. No. 10/516,049, mailed Dec. 12, 2007.
Reply Brief, filed in U.S. Appl. No. 10/516,049, submitted Feb. 12, 2008.
BPAI Decision, U.S. Appl. No. 10/516,049, Mar. 24, 2009.
Request for Rehearing of BPAI, filed in U.S. Appl. No. 10/516,049, submitted May 22, 2009.
Decision on Request for Rehearing of BPAI, filed in U.S. Appl. No. 10/516,049, mailed Jun. 23, 2009.
Office Action, issued in U.S. Appl. No. 12/536,243, mailed Jun. 8, 2010.

* cited by examiner

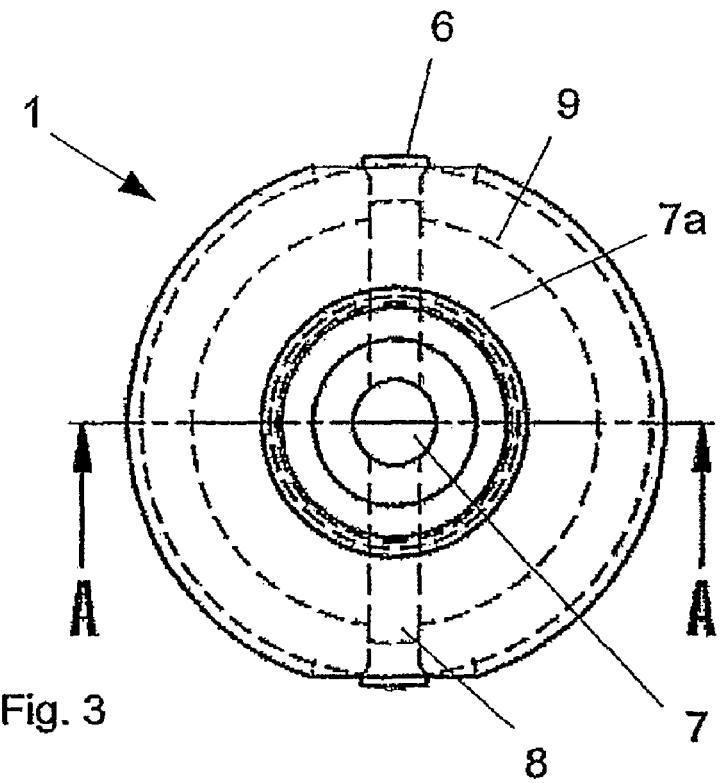
Fig. 3
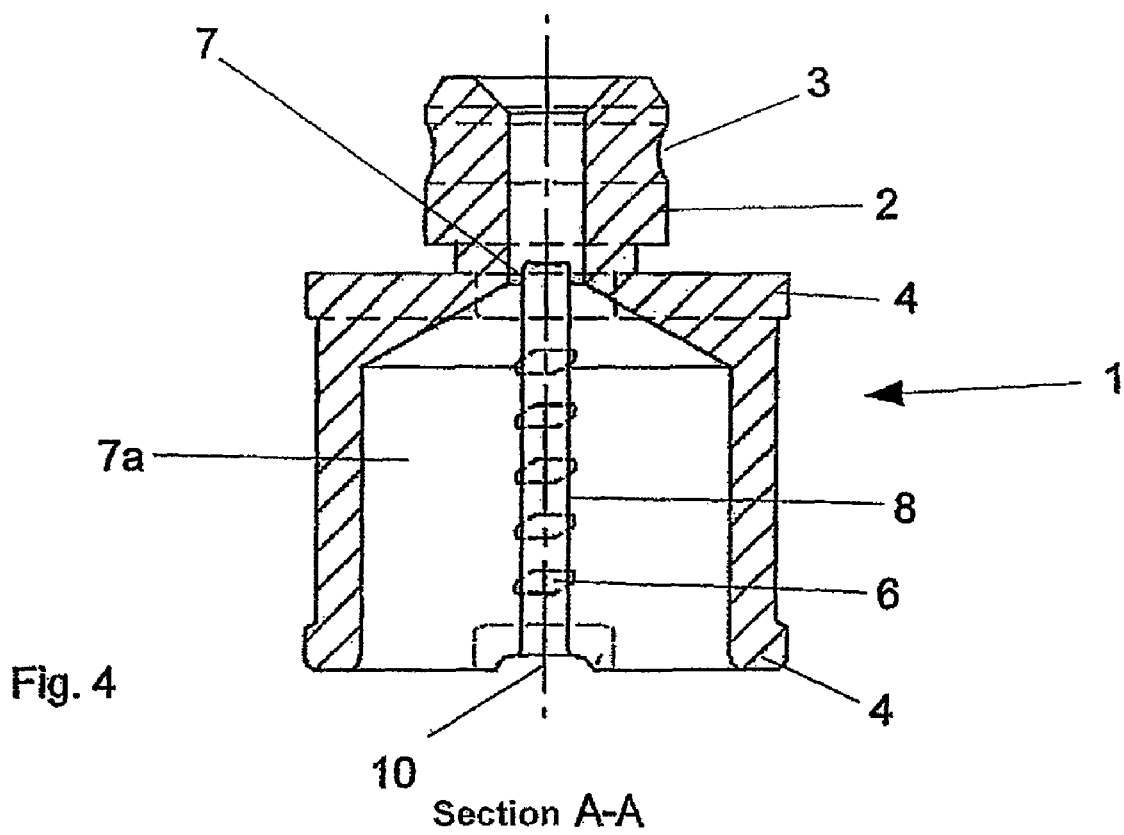
Fig. 4  Section A-A

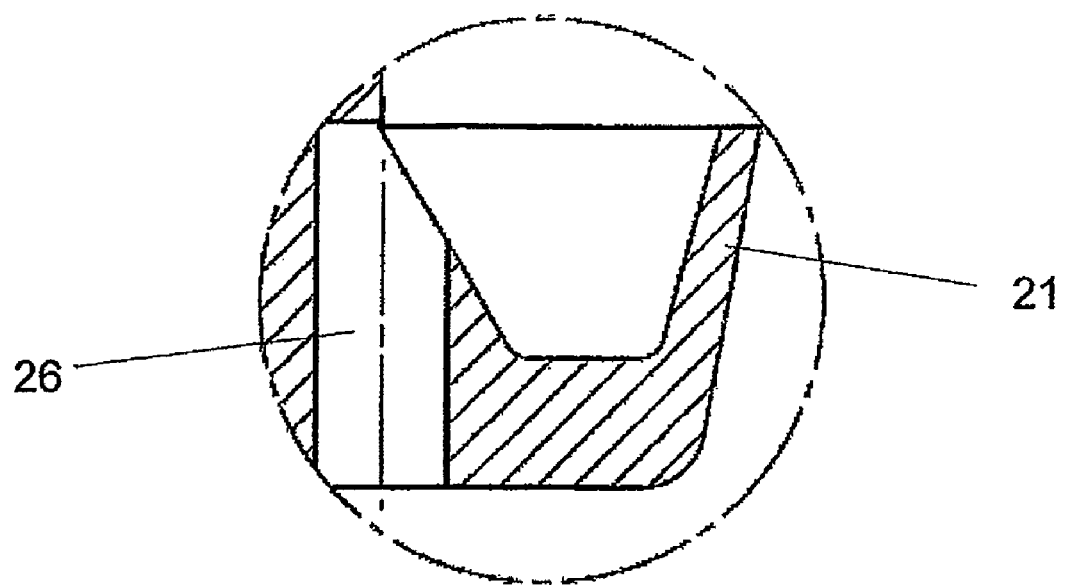
Fig. 12  Detail B
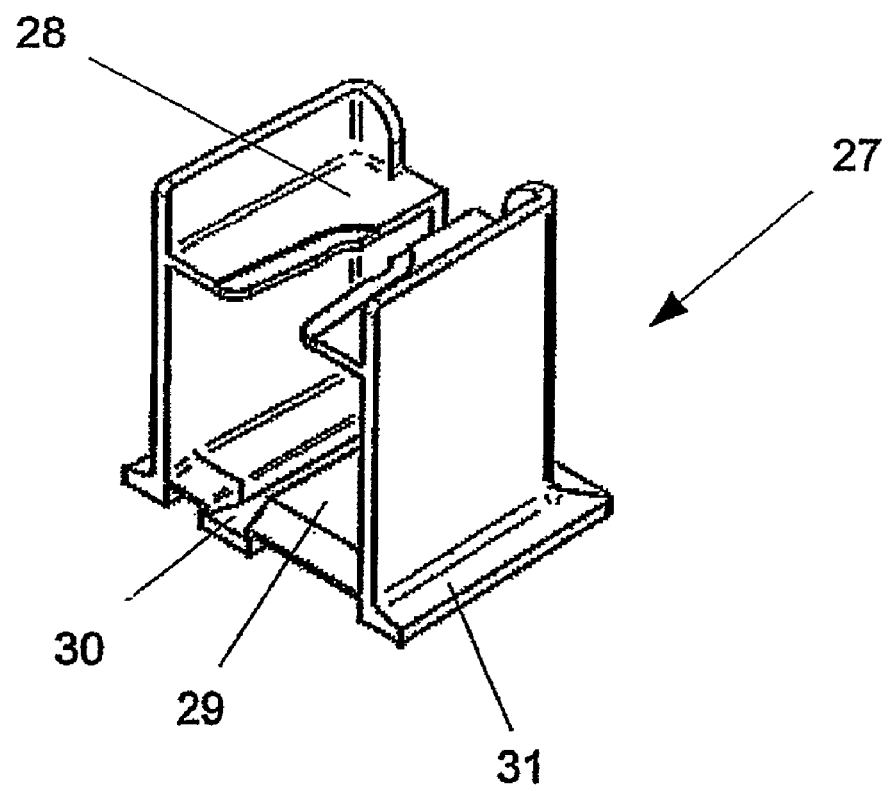
Fig. 14

Section A-A

Section B-B

Section C-C

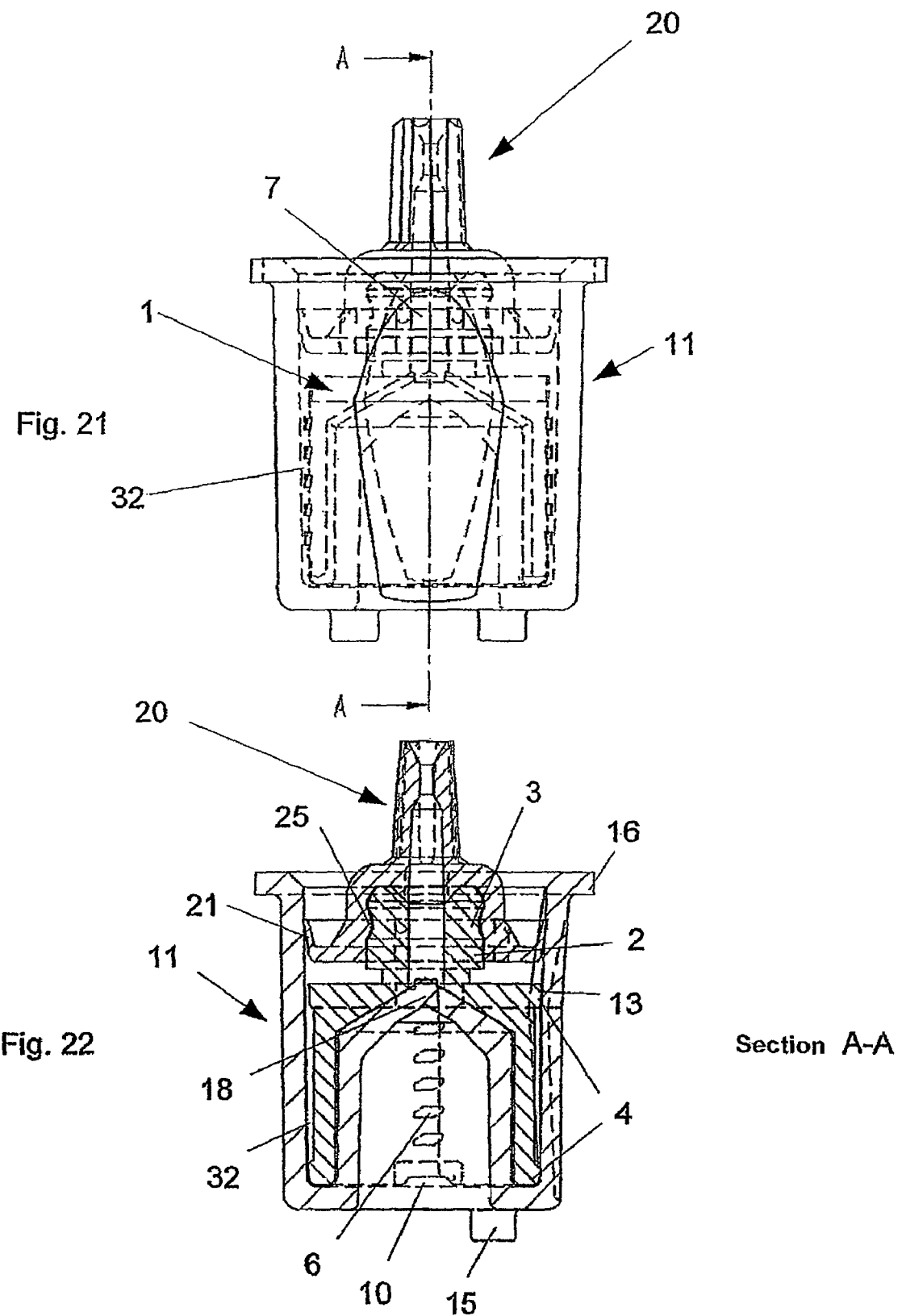

Section A-A

DEVICE FOR THE ANALYSIS OF LIQUID SAMPLES

This application is a national phase application under 35 U.S.C. §371 of International Application No. PCT/AT2006/000411 filed 9 Oct. 2006, which claims priority to Austrian Patent Application No. A 1641/2005 filed 7 Oct. 2005. The entire text of each of the above-referenced disclosures is specifically incorporated herein by reference without disclaimer.

The present invention relates to a device for the analysis of liquid samples.

Because of the enormously many different biomolecules and their different appearances (chemical modifications) and variants (DNA-sequences), high-through-put technologies are increasingly used. In addition to classic methods, Northern and Southern blotting, in-situ hybridisations and any kind of Westernblot techniques, multi-analyte detection systems have increasingly been developed during the last 15 years. The most important ones of these systems use mainly microtiter plates (e.g. as standard carrier for ELISA) with several hundred analyses per passage and microarrays with more than 100 analysis points per $cm^2$. The DNA-arrays which are described in U.S. Pat. Nos. 5,800,992 and 5,744,305 by Fodor et al. and based on oligonucleotides are known, and the microarrays which are disclosed in U.S. Pat. No. 5,807,522 and based on c-DNA are known. Current microarrays operate with binding partners (sensor molecules) applied on solid carriers in certain areas, which binding partners constitute at least one binding site for components (analytes) of a sample to be analysed, or interact with components of the sample. In this context, the binding partners are, e.g., distributedly arranged across the carrier in a certain pattern ("array"), wherein the carrier itself always has a planar geometry (e.g. U.S. Pat. Nos. 5,800,992 and 5,744,305). The respective analyte detection is based on a molecular binding of components of a sample with the sensor molecules. Thus, it can be detected whether certain components are contained in a sample by finding out whether such components have entered into a bond with the immobilised binding partners. The detection of such a molecular binding is done, e.g. by means of an optical (e.g. fluorescence, luminescence, surface plasmon resonance spectroscopy), an electrochemical measurement or the measurement of a change in the mass of the molecules located on the sensor.

Current microarrays are almost exclusively used in research and development, wherein there has also been increasing interest in diagnostic applications.

All applications share the object of bringing substances which are unknown and dissolved in a mostly aqueous sample liquid into contact with binding partners known and immobilised on a solid support. A substantial prerequisite for a suitable interpretation of the signals developed after the contact is the equal treatment of all binding partners applied on the carrier. This object is of increased importance if the concentration of the sample components is very low and/or if, for signal generation, different temperatures have to act on the detection system in a different order and for different periods of time. In particular in the latter case, unsolved problems result from temperatures of up to 100° C., including formation of gas bubbles, temperature differences along the incubation area, evaporation problems and differences in concentration occurring as a consequence thereof. When examining proteins which are capable of entering a reaction with certain gases, what affects their activity such that a reasonable measurement is no longer possible, the current systems (e.g. conventional protein arrays) involve the danger of a temporary undesired contact with ambient air and/or non-defined gas mixtures. Only a closed incubation room could provide controllable and constant conditions of incubation. Furthermore, the major part of the existing systems does not allow for continuous measurement of the interaction between the binding-partner molecules and the sample molecules without opening the testing device. If it is opened, the development of these interactions is interrupted and, due to reassembling of the testing device (cf. incubation chambers of, e.g. the following providers: Corning, Genomic Solution, BioRad, Takara Bio, Advalytix, Genetix, Gesim; the incubation chambers are mostly reusable and have a shell-shaped structure, wherein there is a planar carrier within the chamber closed by sealing webs), the examination cannot be continued without serious consequences. The consequence is an end-point measurement, i.e. the measurement is done after all steps of incubation and provides one measured value per binding partner. The situation is comparable with the application of the polymerase chain reaction and the subsequent analysis of the products and the corresponding further development of the real-time polymerase chain reaction. Only the progressive measurement (continuous measurement) meets the prerequisites for a sufficiently exact quantity measurement and for use in in-vitro diagnostics. The device described in WO 01/25759 and WO 01/53822 is an exception. This array system allows for continuous measurement of interactions occurring on the surface of a planar carrier without opening the arrangement of the incubation unit. This system, however, has the disadvantages of complex microfluidics by means of external pumps which have to be cleaned after every sample, which roll the sample liquid across the carrier surface in an external cycle and which, thus, may not provide for a constant temperature of the sample liquid, and of an inconstant radiation with electromagnetic waves (excitation light) caused by the asymmetric optical path. A further device is the so-called hollow mini cylinder (DE 198 28 837 A1). This system is similar to the use of spatial carriers which are used in spherical form as a stationary phase. Moreover, it is known from WO 03/100401, WO 00/40334 and WO 02/08457 that a carrier in cylindrical form, on its surface, has immobilised binding partners in defined areas (spots) and may perform the incubation of the sample liquid by the immersion method in a complementary sample container under tempered conditions. A measuring unit is assigned to the sample container which may detect possible interactions.

The devices described have, among others, the disadvantage that contaminations may be introduced into the sample container itself or that an evaporation of the liquids introduced into the device may occur during examination due to the mostly small sample volumes used during examination. Changes in concentration of the individual sample components result therefrom, whereby the measurements may be influenced negatively. One further disadvantage of such devices, in particular of such a device as described in WO 03/100401, is the unstable and non-axially centred mounting of the rotor during its rotational movement. These mounting complications may result in that the rotor temporarily contacts the inner wall of the sample container and that, thus, the annular gap provided between the rotor and the sample container varies during measurement (leads to skewed measurement results), and the binding partners which may be present on the rotor or on the inner wall of the sample container are subjected to mechanical stress and may, thus, change their binding properties.

Thus, it is an object of the present invention to provide for devices for the analysis of samples, said devices being comprised of a sample container and a rotor insertable thereinto, in a manner that small sample volumes may be inserted and the danger of contaminations and the problem of possible evaporation processes is reduced or eliminated. A further object is to provide for a device for the analysis of samples which is comprised of a sample container and a rotor insertable thereinto and allows for an improved mounting of the rotor in the sample container.

This object is achieved by providing a device for the analysis of liquid samples, comprising a rotational-symmetric rotor insertable into the sample container, wherein an annular gap is provided between the sample container and the rotor, and the rotor has at least one flow channel for transporting liquids and/or gases into and/or from the interior of the sample container, wherein means for centred mounting of the rotor are arranged on the rotor and, optionally, on the sample container.

The device disclosed herein comprises a rotor and a sample container. Between the rotor and the inner wall of the sample container, a radial annular gap is provided which defines the incubation room (the space in which the binding partner and the ligand may react and/or interact). According to the invention, the rotor has a flow channel, through which liquids can be transported into the sample container or removed from the sample container. The means provided on the rotor and in the sample container for centred mounting of the rotor in the sample container allow a stable and centred mounting of the rotor in the sample container. Thus, it is prevented that the rotor comes into contact with the sample container during the rotation of the rotor or the sample container. Such an unbalanced rotation results in a quick wear of the device parts, on the one hand, and in an adverse effect on the bond between binding partner and ligand, on the other hand. Furthermore, due to the changing annular gap (distance between the rotor and the sample container), which results from an unbalanced rotation, the measurement result of the detection of the bond between binding partner and ligand will also be negatively influenced, since the volume of the annular gap and, thus, of the incubation room, will change correspondingly.

The means for centred mounting on the rotor and the sample container may be connected positively (e.g. elevation-dent, bearing pin-bearing sleeve, etc.).

According to a preferred embodiment of the present invention, at least one elevation is provided on the jacket surface of the rotor and/or on the inner wall of the sample container.

Arranging at least one elevation on the jacket surface of the rotor or on the inner wall of the sample container has the effect that the solutions present in the inventive device are intermixed better during rotation of the rotor or the sample container because of turbulences. In this context, the elevation may be of different shapes, wherein it is, however, preferred to design the elevations such that a good intermixture is allowed for without a negative effect on the detection of the bond between binding partner and ligand.

In order to transfer a torque to the rotor, the inventive rotor comprises means for transferring a torque to the rotor.

In order to put the rotor into rotation by a suitable device, means are provided on the rotor which allow for the transfer of a torque to the rotor. Here, the sample container correspondingly has means which fix the same radially. Thus, it is prevented that the sample container will also be put into rotation due to frictional effects occurring during rotation of the rotor. It is also within the meaning of the present invention to fix the rotor radially and to put into rotation the sample container itself. In this case the sample container has means for transferring a torque to the sample container, and the means provided on the rotor for transferring a torque serve as fixing means.

According to the present invention, "fixing radially" shall be understood as providing for means which are used to prevent the rotor and/or the sample container from its rotational movement.

Preferably, the means for transferring a torque to the rotor is a longitudinal body which extends axially to the rotor.

According to the invention, it has been shown that a longitudinal body which extends axially to the rotor is particularly well-suited for transferring a torque to the rotor. In this context, the longitudinal body may have any geometric ground plan, yet an n-angular ground plan (n is selected from 3, 4, 5 and 6, e.g.) is preferably used. Furthermore, means may be provided on the longitudinal body which facilitate positive and/or non-positive connection with a torque-generating device (e.g. the longitudinal body may have axial elevations and/or projections or recesses and/or dents).

According to a preferred embodiment, a lid for covering the interior of the sample container is provided on the rotor or on the sample container.

A lid for closing and covering the sample container has several advantages. It allows for keeping the interior of the sample container free of contaminations (e.g. excluding dust and microorganisms), on the one hand, and for minimisation or complete exclusion of evaporation processes within the sample container, on the other hand. According to the invention, the lid may be provided in a way that it has a diameter which is at least or substantially the one of the opening of the sample container. If the diameter of the lid is larger than this opening, the lid will project beyond the rim of the sample container, if the diameter is smaller or substantially the same than/as the one of the sample container, the lid will close the lid of the sample container within the container.

A further aspect of the present invention relates to a device for the analysis of liquid samples, comprising a rotational-symmetric rotor insertable into a sample container, wherein an annular gap is provided between the sample container and the rotor, the rotor has at least one flow channel for transporting liquids and/or gases into and/or from the interior of the sample container, and at least one elevation is provided on the jacket surface of the rotor or on the inner wall of the sample container, wherein a lid for covering the interior of the sample container is arranged on the rotor or on the sample container.

This inventive device comprises a rotor, a sample container and a lid which delimits the interior of the sample container relative to the ambience, the rotor being provided in said container, when inventively using the device. The upper region of the rotor may, e.g., itself be designed as lid (e.g. by providing a projection on the rotor which can be introduced into the sample container or which rests on the sample container), or the lid is attached to the rotor. The rotor is provided with a flow channel through which the sample liquid and other liquids or gases necessary during analysis (e.g. incubation solutions, buffers, detection solutions, wash solutions, inert gas) may be introduced into the interior of the sample container. Thus, the flow channel is the connection between the ambience and the interior of the sample container. Advantageously, the flow channel can be connected with a distributing device (e.g. pipetting robot) for gases and liquids. Because of the use of a corresponding distributing device, the inventive device is also suitable for use in high-throughput screening. Moreover, the device can also be used as a disposable analysis device.

At least one elevation is provided on the rotor or on the inner side of the sample container. This elevation serves for efficient intermixing of the solutions present in the radial annular gap between the rotor and the sample container, since the solution itself will be put into radial movement during the radial movement of the rotor, and the elevation provided will cause turbulences in this solution, resulting in an efficient intermixture of one or several solutions. If more than one elevation is provided on the rotor or on the inner side of the sample container, these elevations may be arranged in the most different ways. For example, the elevations may be arranged axially, spirally, or in any other way, along the rotor or the sample container.

Suitable analysis devices which, according to the invention, can be provided with a lid, are disclosed in WO 03/100401, e.g. In order to avoid, in particular, contaminations of the inventive device and to reduce or prevent an evaporation of the sample liquid out of the inventive device, a lid is inventively attached to the above-disclosed device.

According to the present invention, the "lid" (as mechanical barrier) is that delimitation of the sample container that closes the latter's opening on the side opposing the bottom of the sample container. The lid is of a material which is inert relative to the gases and liquids used with the device and is substantially liquid-impermeable and gas-impermeable. The lid has a diameter designed such to introduce the lid into the sample container or to mount it on the rim of the opening of the sample container. In the latter embodiment, the lid has a radial recess on the side of the lid facing the sample container, said recess having the same diameter as the sample container on the contact surface lid/sample container. Thus, the lid can be mounted on the sample container.

In order to allow for the escape of the gases expelled by the liquid in the case of a closed system which comprises a rotor, a sample container and a lid with a flow channel for introducing liquids into the sample container, at least one opening may by provided on the lid. Without such an opening and without no suitable openings provided on the sample container or on the rotor and without an air-impermeable and liquid-impermeable design of the interior of the sample container, a pressure would build up in the sample container during introduction of liquids which would be such high that introducing further liquids would be hardly possible. This can be prevented by an opening preferably provided on the lid without substantially affecting the protective function of the lid. Of course, it is also possible to fill the sample container with corresponding solutions (e.g. sample solutions, incubation solutions, detection solutions) prior to analysis, and to thereafter put the rotor into the measuring position (by immersing the rotor into the sample container).

Preferably, means for centred mounting of the rotor in the sample container are provided on the sample container and on the rotor.

In order to stably mount the rotor together with the lid in the sample container and to allow for a balanced centred rotation, the inventive sample container and the inventive rotor have means for centred mounting.

The following embodiments relate to substantially all aspects of the present invention.

According to a preferred embodiment of the present invention, the means for centred mounting of the rotor in the sample container are an elevation or dent oriented towards the interior of the sample container and located on the bottom of the sample container, and a recess provided on the rotor being complementary thereto.

This elevation or dent serves for radially movable mounting of the rotor in the inventive sample container, whereby a secured centring and/or positioning of the rotor in the sample container is rendered possible. These elevations or dents may be of any design (e.g. bearing pins—bearing sleeves). It is absolutely possible to provide further bearing elements in the elevation or dent so that the rotor is mounted in the sample container by means of a ball-bearing. Alternatively, it is also feasible to introduce an insert into the bottom of the sample container, said insert having a dent or elevation which is complementary to the elevation or dent on the rotor. In case of such an embodiment, the bottom of the sample container could not have elevations or dents.

Furthermore, a recess may be provided on the bottom of the sample container, into which a complementary elevation located on the rotor and/or a complementary pin located on the rotor may be introduced for centred mounting.

According to a preferred embodiment of the present invention, the elevation or dent has a cylindrical form, conical form, frustoconical form, or a combined form thereof.

Particularly these geometric designs have proven to be particularly suited. According to the invention, of course, also at least one radial elevation or recess (symmetrically about the rotational axis of the rotor) provided at the bottom of the sample container and a corresponding complement provided on the rotor may serve as means for centred mounting.

Preferably, the flow channel of the rotor is connected with the means for centred mounting of the rotor, that is, the bearing means itself serves as a flow channel in this preferred embodiment. Thus, the solutions which are introduced into the sample container in case of such a device are transported between the bearing means of the sample container and the bearing means of the rotor (=flow channel).

On the inner side of the means for centred mounting of the rotor, preferably at least one depression is provided which extends along the means and/or the flow channel.

Providing such depressions along the means for centred mounting and along the flow channel is of particular advantage when using the inventive device for analysing small amounts of samples; because of this depression the sample liquid is allowed to flow into the sample container along this depression. Furthermore, such a depression is advantageous if, e.g. an elevation for mounting the rotor is provided within the sample device, and if the means which is provided on the elevation and is complementary thereto abuts the rotor, in its function as flow channel of the rotor. Without such a depression, this elevation would complicate or prevent a flow of the sample liquid or other liquids into the sample container. According to the invention, the receiving means and/or the flow channel may have only one but also several such depression(s) (e.g. at least two, at least three, at least four, at least five, at least six, at least ten).

Preferably, at least one recess is provided in the lower region of the rotor, which recess allows for a liquid passage from the receiving means and/or flow channel of the rotor into the sample space (radial gap between the rotor and the sample container) when the rotor has been fully introduced into the sample container. Preferably, this recess is part of the at least one depression in the flow channel of the rotor.

A repeated change in temperature of the incubated liquids is necessary for several chemical detection methods and biochemical conversion reactions (e.g. polymerase chain reaction, ligase chain reaction, primer extension, digestion of nucleic acids with thermostable nucleases). In this context, the accuracy of these changes in temperature is of essential significance. In order to control the liquid within the inventive device, a thermoelement may be inserted into the dent provided in the sample container, wherein the dent has to be designed such that it receives elements of this kind. Preferably, this thermoelement consists of a cooling system (e.g. Peltier element) and a heating system (e.g. infra-red heater, microwave heater or Peltier element). In this context, the thermoelement may be preferably of such a design that it allows for positioning of the inventive device in a measuring unit or in a cartridge. Thus, the dent is preferably designed for receiving a cooling and/or heating device. Furthermore, the advantage of such an embodiment is that, in addition to controlling the temperature of the sample liquid, the inventive device and/or the sample container may also be positioned. Of course, temperature control may be effected via the side wall or the bottom of the sample container as well (cf., e.g. WO 03/100401).

Preferably, the dent comprises means for transferring a torque to the sample container and/or means for fixing/positioning of the sample container.

Preferably, such a means for fixing of the sample container and/or for transferring a torque to the sample container is a longitudinal body (e.g. pin or bolt) located in the dent and arranged axially to the rotor, wherein a radial gap is provided between the longitudinal body and the outside of the dent. This longitudinal body may be introduced into a further device by means of a corresponding complementary part (e.g. depression, gripping device), said further device being capable of receiving the inventive device.

According to the present invention, a torque may act on the analysis device not only via the lid, but it is definitely also possible to fix the lid together with the rotor and to put into rotation the sample container itself. Here, according to the invention, a detection system may be incorporated into the sample container and/or the receiving element (e.g. the means for centred mounting of the rotor in the sample container) of the container may contain a detection system. Of course, it is also possible to provide the rotor itself with a detection system.

According to a preferred embodiment, the means for centred mounting is a magnetic bearing, wherein the magnetic bearing is preferably illustrated such that magnets are provided on the rotor and, optionally, on the sample container.

Magnetic bearings allow for mounting of the rotor in the sample container substantially without contact of the material via magnetic force. In this context, a first magnet can be provided on the rotor, and the second magnet can be provided on the sample container or in a further device (e.g. into which the inventive device for measuring is inserted) or retaining element. Preferably, the magnets provided on the rotor are arranged annularly at the bottom of the rotor or in its vicinity. Preferably, the magnets used in the rotor are permanent magnets, and the magnets provided in the sample container and/or further device may not only be permanent magnets but also electromagnets.

In order to measure and detect the binding reactions occurring in the sample container, the sample container is preferably at least partly transparent.

The detection of the developing interactions between the binding partners and the ligands to be bound within the inventive device can be done in various ways. The principle used most for detecting such interactions is the measurement of electromagnetic waves, in particular of fluorescence, chemoluminescence, bioluminescence, fluorescence resonance energy transfer (FRET), which are generated by the bond of corresponding marker molecules (e.g. labelled binding partners) to the ligands immobilised on the rotor by binding partners. Here, it shall also be possible to continuously measure interactions between binding partners and ligands present in the sample liquid. With respect to the measurements done on the sample container it is important that the incubation process itself is not disturbed by the measurement, and that an interruption of the measuring procedure (e.g. by exchange of solvents, changes in temperature) must not occur with successive steps of a different kind either.

If the detection of molecules on the surface of the rotor shall be done by means of fluorescence, it is advantageous if the molecules to be detected or the molecules being in competition with the molecules to be detected have been labelled with an appropriate substance (e.g. with a fluorophore or a quencher and/or molecule groups which interfere with electromagnetic waves). For example, if a DNA-molecule is inserted, detection may be effected directly via integration of fluorophore-labelled nucleotides. On the other hand, if detection shall be effected indirectly via further secondary binding partners, there is also the possibility to label the molecules with markers, such as, e.g. biotin, digoxigenin (DIG).

The inventive device is preferably suited for measuring chemoluminescence reactions, wherein the light emission of a substrate soluble by an appropriate enzyme (e.g. peroxidase) is measured. In this context, the detection of such a conversion can be done in different ways. For example, so-called CCD cameras ("charge-coupled device" cameras) may be used, as they are described in U.S. Pat. No. 5,173,748, WO 03/014400. The measurement can be done, e.g. using the so-called TDI mode ("time-delayed integration" mode). This mode requires a synchronisation of the reading speed of the CCD used and the movement of the object to be observed (e.g. microarray, biochip or rotor of the inventive device) (cf. WO 03/014400). According to the present invention, wherein the binding partners are preferably coupled on the surface of the rotor, they are synchronisedly rotated past the measuring system via the rotational speed as seemingly lateral movement. Alternative to CCD cameras, photo multiplier arrays (e.g. PMT (photo multiplier tube), APD (avalanche photo diode)) can be used.

Besides the above-described optical measuring system using lenses, optical sensors without lenses may also be used according to the invention. In this embodiment, the measuring system (e.g. photo diode array) may be designed as a disposable product, as a combination with a sample container, or may be a regular component of the heating system located on the sample container. Since the rotor (binding-partner carrier) and, thus, also the sample container preferably have a cylindrical form, the requirement of a curved design of the photo sensor is of particular significance. In this context, particularly amorphous silicon diodes or photosensitive polymer layers are suited, as they are described, e.g. in WO 03/015189 and WO 01/84644). The use of silicon photo diodes in spatial vicinity to the surface of the sample container is particularly advantageous for the use of chemoluminescence detection methods, since they can be employed without any additional light source for excitation of light emission for detection of the interactions occurred between the binding partners and the ligands in the sample liquid. A further possibility is, e.g. the use of light sources, for example inside a dent which projects into the sample container. Here, the kind of light source may be a direct one, i.e. a unit with the carrier, or an external one which is used for illuminating and/or exciting marker molecules in the sample liquid. Furthermore, so-called light-emitting photosensitive diodes may be used. In this embodiment, a combination of illumination and detection is the case. Compared to usual measuring systems, the advantage is that external light sources, optical components and external detection systems, such as, e.g. CCD cameras, are not at all necessary. The spatial arrangement of the measuring system in the device would change correspondingly. In this context, the diodes are preferably positioned as close as possible on the sample container. Here, the detection is done without optical lenses and other systems directly via the occurrence of photons in the direct vicinity of the place of development.

Preferably, the detection system described in US 2002/177144, WO 00/79326, WO 00/62549, WO 00/25113, WO 00/12759, WO 97/12030, U.S. Pat. No. 5,585,639, US 2002/066865 and EP 0 947 824 are used for the inventive device.

The object of the continuous and/or step-wise (after change in time, liquid or temperature) optical illustration of a jacket surface through a liquid film which, in turn, is produced by filling the radial annular gap (cf. present invention and, e.g. WO 03100401 A1) is achieved in that observation (preferably measuring the electromagnetic radiation emitted from the surface of the jacket surface indicated) is effected by means of a transparent container, wherein the measuring system consists of, e.g. a CCD camera or an APD (avalanche photo diode) or a comparable detection system which is oriented relative to the jacket surface in a substantially normal way and represents a strip surface of the jacket surface indicated. The measuring system is connected with the rotational unit such that the rotational speed and the exposure time can be harmonised with each other. The thus synchronised illustration can optionally be employed when using the so-called TDI mode. Here, the step-wise rotation is timely synchronised with the integration time of the CCD chip. The result is the line-dependent addition of signal strength.

Additionally, an illuminating unit may be assigned to the measuring system, which unit preferably consists of an opto-semiconductor (LED) and, alternatively, of at least one laser, a white-light lamp, a gas-discharge lamp, UV or IR lamp. Furthermore, a lens system consisting of at least one collecting lens, at least one filter set and/or a infra-red filter may be assigned to the measuring system.

The advantage of such devices resides in that measurement can be performed at any time without causing a change in the reaction conditions, a break and/or opening of the incubation room.

According to the invention, the sample container may consist completely or only partly (e.g. providing inspection windows) of a material which is suited, e.g. for photometric measurement, and transparent.

This inspection window (or the area in which the analysing device measures) may adapt the form of a lens (or of lens structures) for optimising the optical properties. Thus, a focussing of the incident and emitted light and, thus, a higher yield of the measuring signal can be achieved.

According to a preferred embodiment, the flow channel of the rotor is arranged axially.

In order to introduce sample and/or wash and incubation solutions into the sample container, the rotor has a flow channel through which, from the outside, liquids may be introduced into the device. Here, preferably, the flow channel is arranged axially on the rotor. Of course, it is also possible to provide the flow channel with any course and any branches within the rotor and any outlet site in the sample container. Furthermore, preferably, an outlet is provided in the lower region of the rotor.

Preferably, the diameter of the flow channel of the rotor is larger in the region of the bottom of the sample container than in the region of the opening of the sample container.

The diameter of the flow channel of the rotor may increase in the direction of the bottom of the sample container (e.g. in a linear or cascade way). A linear or cascade enlargement may correspondingly increase the bearing surface, whereby the concentric mounting and, consequently, the accuracy of measurement may be improved. Moreover, the increase in the diameter of the flow channel of from, initially, 1-2 mm to 10-15 mm allows for the introduction, as e.g. described above, of a heating and/or cooling system into the bearing means of the sample container. The reduced wall thickness of the rotor reduces the material needed, on the one hand, and may facilitate and improve the production process, on the other hand (e.g. injection-moulded process: better injection and faster hardening).

According to the invention, the lid is detachably attached to the rotor.

According to a further preferred embodiment of the present invention, the lid may be detachably attached on the rotor, whereby it is rendered possible to, e.g. reuse the lid. Of course, it is absolutely possible and in the meaning of the invention to provide the lid in a way fixed to the rotor and/or to provide the rotor and the lid as an integral part.

Preferably, the lid has a flow channel which is arranged in series relative to the flow channel of the rotor and connected therewith.

After filling the inventive device with sample liquid or other liquids, the device can be closed by means of a lid which is attached to the rotor. In order to simplify this procedure and to make it more efficient and, moreover, to reduce the risk of contaminations even more, the lid of the rotor has a flow channel itself which is connected with the flow channel of the rotor. Thus, it is rendered possible to at first prepare the device including rotor and lid and to then introduce the liquids which are to be introduced into the device directly into the device through the lid. Providing a flow channel in the lid is of particular advantage when using the inventive device as flow-through cell.

Preferably, the flow channel of the lid has a smaller diameter than the flow channel of the rotor.

By such a reduction in the diameter of the axial flow channel (rotor and lid) combined with a pressure-proof connection, a backflow of the sample liquid into the liquid-distributing device can be substantially eliminated.

According to a preferred embodiment of the present invention, the lid has a sealing lip on its rim.

In order to efficiently seal the interior of the device, the lid comprises a sealing lip. This sealing lip which extends across the entire outer rim of the lid prevents the flow-off of liquid via the radial gap between the rotor and the sample container and, additionally, serves as a gas barrier which may pre-vent contact of sample liquid and, e.g. atmospheric oxygen. This is particularly advantageous if samples are to be examined which react to gases, e.g. oxygen, and may thus skew the measurement result. Furthermore, arranging a sealing lip on the lid renders it possible to provide for a certain atmosphere within the device. Thus, e.g. nitrogen can be introduced into the sample container, allowing for carrying out analyses under protective atmosphere. Such examinations are of particular interest when it comes to analysing, e.g. oxygen-sensitive samples. Thus, the inventive lid which may be put onto an inventive rotor or is integrally produced therewith is of advantage particularly as regards protection against contaminations, evaporation and oxidation.

According to a further preferred embodiment of the present invention, means for transferring a torque to the rotor connected with the lid are provided on the lid.

In order to radially move the rotor in the sample container, it is necessary to transfer a torque either to the rotor itself or to the sample container. It has proven to be advantageous to effect this transfer via the rotor. Therefore, preferably on the lid, there is provided a means for transferring the torque generated by a torque-generating device (e.g. electric motor (stepper motor, direct-current motor, alternating-current synchronous motor, alternating-current asynchronous motor), combustion engines, gas turbines, etc.) to the rotor.

The means for transferring a torque to the rotor is preferably formed by a longitudinal body which extends axially to the rotor.

The means responsible for transferring the torque to the rotor can be of different design, wherein, preferably, the means for transferring is a longitudinal body. A longitudinal body has the advantage that the device for generating a torque is provided with a contact point on the lid, wherein the longitudinal body preferably has an angular shape (n is preferably selected from 3, 4, 5, 6 or 7). In the meaning of the present invention it is also advantageous to provide for a longitudinal body which has axially (along the longitudinal body) extending elevations (at least one elevation) serving as a contact and/or fastening point for the torque-generating device.

According to a preferred embodiment, the rotor comprises fastening means for fastening of the lid.

In order to fasten the lid on the rotor both axially and radially, the rotor comprises a fastening means on its upper region. Here, the fastening means may either be integrally produced with the rotor or the fastening means is attached to the rotor.

Preferably, the fastening means are formed by at least one radially arranged elevation.

In order to fix the lid to the rotor, it has turned out to be advantageous to provide for a fastening means in the form of an elevation on the rotor. The elevation may have a diameter reducing towards the free end.

According to a preferred embodiment of the present invention, the elevation is provided with a spiral-shaped notch (winding), a radial recess or a radial projection.

Correspondingly, the lid preferably has a dent for receiving the fastening means, wherein according to a preferred embodiment the dent itself has spiral-shaped notch (winding), a radial projection or a radial recess for fixing the fastening means of the rotor in the dent of the lid.

It is advantageous if the elevation of the rotor used for fixing the lid has a spiral-shaped notch, a radial recess or a radial projection. Thus, it is rendered possible in a simple manner to provide for a lid with a dent for receiving the fastening means of the rotor, wherein the dent is the counterpart of the elevation and, thus, also comprises a spiral-shaped notch, a radial recess or a radial projection. By providing spiral-shaped notches and/or radial projections and radial recesses, the lid may be fixed to the rotor in a preferably detachable way.

According to the present invention, it is particularly preferred to fix the lid to the rotor by means of a snap-in device. Here, the lid which has elevations and/or dents on the contact surface to the rotor snaps in the same since corresponding complementary elevations and/or dents are provided on the rotor.

According to a preferred embodiment of the present invention, at least one binding partner for binding of at least one ligand is provided on the rotor and/or on the inner side of the sample container, wherein the at least one binding partner preferably is a biomolecule, in particular an antibody, an antigen, a haptene, a peptide, polypeptides with diverse prosthetic groups, enzymes, hormones, a nucleic acid or derivatives thereof, e.g. peptide nucleic acids.

The inventive device is primarily suited for analysing interactions between proteins, nucleic acids and other biological molecules, such as, e.g. membrane components, lipids, hydrocarbons and derivatives thereof, carbohydrates, haptenes, hormones and synthetic active substances (e.g. growth inhibitors such as antibiotics, pesticides, herbicides or fungicides, or inhibitors and/or activators of biochemical metabolic reactions), wherein at least one of the binding partners is bound to a stationary phase in a covalent or non-covalent manner, or as a sandwich via the general adapter, and is contacted with the components of the sample container to be analysed via a liquid-guiding system and their interactions are detected by means of a detection device. The kind and number of the biomolecules detected in a sample allow for, e.g. clear conclusions as to the presence of viral, bacterial, eurocaryotic, in particular animal or human, DNA or to the presence of different forms of proteins (phosphorylations, glycosylations) or nucleic acids (methylations) or also lipids with possible glycosylations.

In order to analyse the samples and to detect their components and/or to bind ligands to the rotor and/or to the inner side of the sample container or to isolate them, using the inventive device, corresponding binding partners are immobilised on the rotor and/or the sample container. The binding partners used in this context are selected corresponding to the ligands to be bound. Thus, for example biomolecules such as, e.g. antibodies, nucleic acids, sugar chains, lectins or other proteins, can be immobilised on the rotor to bind ligands (which are also binding partners) to the immobilised binding partners. Alternatively, the ligand may also be bound to the rotor and/or the sample container so that in this case the ligand per definitionem (in the meaning of the present invention) is referred to as binding partner.

The inventive device is not only suited for detecting certain substances in a sample but also for converting substances, thus allowing for, e.g., enzyme kinetics to be received. Furthermore, the inventive device may be used for carrying out enzyme reactions, such as, e.g. DNA-polymerase reactions (solid-phase amplification, arrayed-primer extension (APEX)), DNA-ligase reactions, DNA-methyl-transferase reactions, restriction endonuclease and exonuclease reactions, oxidoreductase, hydrolase, ligase, lyase, isomerase, phosphatase, kinase, methylase and transferase reactions.

Preferably, as spacing element, the rotor has at least one outward-oriented radial projection and/or the inner jacket of the sample container has at least one inward-oriented radial projection.

By providing at least one spacing element, it is possible to create a reaction space between the rotor and the wall of the sample container, wherein this reaction space may be of different size corresponding to the diameter of the rotor and of the spacing element. Moreover, by such an embodiment the binding partners preferably bound on the rotor are protected against mechanical friction with the wall of the sample container. A further advantage of such an element is the improved guide of the rotor when it moves radially in the sample container ("rotor guide"). In this case, the spacing element serves as sort of guide. According to the invention, the rotor may have at least one, preferably at least two, even more preferably at least three, most preferably at least four, in particular at least five, radially outward-oriented spacing elements. Preferably, at least one radially outward-oriented spacing element is located on the lower and/or upper region of the rotor.

According to the invention, it has been proven that a radial projection which may enclose the jacket surface of the rotor without being interrupted is particularly well-suited for being used as a spacing element. In such an embodiment the spacing element also serves as a delimitation for the sample space and/or incubation room.

Preferably, the radial projection has at least one recess, in particular along the depression in the interior of the flow channel.

The recess on the radial projection allows that the solutions introduced through the flow channel may flow from the interior of the rotor outwards into the reaction space between the rotor and the wall of the sample container. The recess may also be designed such that the diameter of the radial projection is reduced.

In alternative to arranging at least one radial projection on the rotor, according to the invention, radial projections may also be provided on the inner side of the sample container. Basically, the projections on the sample container fulfil the same task as the radial projections on the rotor. If binding partners have been immobilised on the inner side of the sample container, the radial projections are preferably provided on the sample container. The projections may also serve as "air-bubble sliders" which may take up possibly developed or introduced air bubbles or particles of dirt from the projections. The consequence is an upward or downward removal or an equal stress on the whole surface and not only on one area as is the case with planar carriers.

In order to allow for a liquid exchange within the inventive device, the radial projection of the sample container has at least one depression, in particular an opening.

According to a further preferred embodiment, the sample container comprises means for its radial fixing in a cartridge.

In order to radially fix the sample container in a retaining element of the device of an analysis device during rotation of the rotor present in the sample container, or to radially fix the sample container in a cartridge (e.g. for transport), a means for radial fixing of the sample container may be provided on the sample container. The means for radial fixing of the sample container in the retaining element or the cartridge is preferably at least one projection provided at the bottom of the sample container, in particular a nodule. Providing a projection on the bottom of the sample container allows in a simple manner for fixing of the sample container in a cartridge and/or retaining element of the device when the latter comprise appropriate means capable of receiving this projection. Thus, the inventive cartridge, which may be part of a measuring unit, serves for receiving the inventive analysis device (sample container, rotor and lid). Thus, the cartridge is a transport and/or storing unit for the analysis device.

According to a preferred embodiment of the present invention, the rotor, the sample container and/or the lid is made of a plastics element, wherein this plastics element preferably is a cyclo-olefin copolymer, polystyrene, polypropylene, polyethylene, acetate polymer, acrylnitrile butadiene stryrene, polymethyl metacrylate, PVC, polyethylene terephptalate, polytetrafluoroethylene, or a combination thereof. Of course, it is possible to design all or certain parts of the inventive device with plastics and also with other materials such as metals (e.g. steel) and ceramics. Thermoplastic plastics such as cyclo-olefin copolymers have proven to be particularly suited. The special feature of cyclo-olefin copolymers is the fact that they have a low expansion coefficient, high chemical resistance, good optical properties (low fluorescence, high transparency) and a particularly good plasticity (e.g. during injection moulding).

Preferably, the surface of the rotor is coated with a metal, preferably a semiconductor metal, a polymer, silicon or a silicon compound with carbon, preferably with graphite, DLC (diamond-like carbon) or diamond, or a combination thereof, wherein the metal is preferably gold, palladium, silver or a combination thereof, and the silicon compound is silicon dioxide. Such modifications allow for a surface definition with, e.g. biomolecules (cf., for example, "Bioconjugate Techniques", G. T. Hermanson (1996), Academic Press Inc., ISBN 0123423368). Gold or similar metal coatings may be produced with PVD (physical gas-phase deposition or physical vapour deposition) or are applied onto a surface by cathode sputtering or PLD (pulsed laser deposition).

Dissolved catalytic si-oxide particles harden to a glass layer above the plastics surface (so-called SolGel technology).

Chemical modification by introducing chemically reactive groups, by epoxy, aldehyde, or plasma treatment for activating the surface layer of the plastics and introducing reactive chemical groups (amino, hydroxy, epoxy, aldehyde, carboxy groups) are preferred methods for surface coating and/or modification.

Preferably, the molecules are bound to the surface via sulphuric compounds (Au—S—R) in combination with a second reactive group as a moiety, preferably an NHS ester or maleimides or similar reactive groups. The corresponding modification of the surface occurs via a chemical immersion process into a DMSO solution with dissolved reagent. Washing with water or apalor solvents, MeOH or acetone or preferably with isopropanole, follows. After drying, the biological binding partners (e.g. antibodies, proteins, peptides, modified DNA, or generally organic molecules which themselves carry reactive groups for covalent immobilisation) are bound to the surface.

A further aspect of the present invention relates to a cartridge for receiving an inventive analysis device, wherein the cartridge has an opening for introducing the sample container and a lateral delimitation provided with a recess, wherein the recess is designed for axial fixing of the rotor.

The use of a cartridge has decisive advantages, particularly during automated use of the inventive device. A cartridge may serve for protecting the sample container including a rotor and a lid against mechanical stress and may, at the same time, serve as packing. Furthermore, the cartridge may be designed such that it is suited for automated filling, e.g. via a magazine with several cartridges, and for definite positioning in a device (e.g. by means of a gripping arm) into which the inventive device can be inserted.

Preferably, the cartridge also has a lateral delimitation provided with a recess, wherein the recess is designed in a way to receive and to radially unmovably mount the upper region of the rotor or the means for transferring a torque to the rotor provided on the lid.

The lateral delimitation provided in the cartridge with a recess has the advantage that this recess may receive either the upper region of the rotor, the lid thus being above the lateral limitation, or the means provided on the lid for transferring the torque, yet without disturbing the radially movable mounting. Such a positioning is of advantage, e.g. in case of an ideal incubation. Thus, it is rendered possible to provide the rotor at different positions within the sample container. For an incubation of certain samples the sample liquid may be brought to a certain temperature before it is used in the inventive device (e.g. for hybridisation) or a further step of sample preparation is carried out which is effected by temperature differences (e.g. PCR). At that point of time there may be no contact with the binding partners on the surface of the rotor yet. This is achieved in that the inventive rotor is not yet completely immersed into the sample container in which the sample liquid is present. Preferably, the lateral delimitation of the cartridge (as horizontal plate) is provided with a recess which covers the entire depth and tapers at the edges such that the radial groove of the rotor can be inserted by applying some pressure and using a provided narrowed portion. As already mentioned above, the lateral delimitation (plate) provided with the recess allows for fixing of the rotor in its relative axial positions to the sample container and for preventing the rotor from lowering into the sample container, thus defining a space, e.g. necessary for pre-incubation. Such a position is also advantageous during transport of the device.

The delimitation (bottom of the cartridge) opposing the lateral delimitation provided with the recess preferably has a depression for receiving the means for radial fixing of the sample container in the cartridge.

With this recess/depression which is substantially complementary to the means for radial fixing provided on the bottom of the sample container, radial movement of the sample container is prevented. Alternatively, the depression may be designed as guiding rail which renders possible reception of the means for radial fixing of the sample container.

A further aspect of the present invention relates to a rotor for an inventive device.

A further aspect of the present invention relates to a sample container for an inventive device.

Yet a further aspect of the present invention relates to a kit for analysing samples, comprising:
  an inventive rotor,
  an inventive sample container, optionally
  an inventive lid, and optionally
  an inventive cartridge.

The inventive kit is particularly well-suited for analysing samples, that is, for determination of ligands in samples, and/or for carrying out chemical and biochemical reactions in the interior of the inventive devices.

A further aspect of the present invention relates to a flow-through cell for analysing samples, comprising:
  an inventive rotor,
  an inventive sample container, optionally
  an inventive lid, and optionally
  an inventive cartridge.

The inventive devices are also particularly well-suited for the use as flow-through cells. Flow-through cells are applied in many fields of analytics. Flow-through cells are particularly suited when there is a repeated change of the sample liquids, incubation liquids, wash liquids and detection liquids during analysis.

In this device the flow channel of the rotor serves as flow-in site which is provided on the upper end of the inventive rotor. The flow-off site, on the other hand, where the liquids present in the sample container may be removed from the same, may be provided on the sample container or on the lid. The flow-through measuring cell itself is defined by the annular gap between the rotor and the sample container, as is the measuring cell of an inventive device which is not adapted as flow-through cell. In such an embodiment it is absolutely possible to omit the inventive lid. An inventive flow-through cell may be used, e.g. for examining larger amounts of sample liquid such as, e.g. water or other samples (e.g. sewage water, cell-culture supernatants), which is moved by the flow-through measuring cell and, thus, is contacted with binding partners preferably applied on the rotor. Here, the measurement may be done in real time, that is, during the flow of the sample liquid through the flow-through cell, the sample is examined by detecting the bond between the substances to be detected and their binding partner immobilised in the device. A further field of application of the inventive flow-through cell is the flow of culture medium through this cell to supply cells growing on the rotor with nutrients and to observe their reaction to changes in the culture medium and, optionally, to analyse, fix and dye the cells.

According to a preferred embodiment of the present invention, at least one opening for flow-off of liquid is provided on the rotor, preferably in a spacing element, or in the lid, preferably adjacent the sealing lip, or on the sample container.

By providing further openings in the device, the liquid introduced through the flow channel may be efficiently removed from the device. Thus, it is not necessary to use the flow channel for both introducing liquids into the sample container and removing liquids therefrom.

The inventive device may be used for a number of applications, processes and methods. These applications include detection of substances in a sample, carrying out enzymatic reactions in the device (e.g. amplifications of nucleic acids), etc. A special method for which the device of the present invention is particularly suited is the detection of substances in saliva.

An object of such a method is the detection of, e.g. illegal substances (drugs) in saliva. Here, a saliva collection is carried out into a sampling liquid. In doing so, the saliva collected is in no way purified (filtration, centrifugation or similar methods). The thus recovered saliva-containing liquid is inserted directly into the inventive device. Here, the following steps are preferably made, wherein, of course, the number and kind of steps may be varied.
  Providing the antibody which acts against the substance searched for (e.g. antigen) (or a labelled antigen)
    For example, in dried form after spraying onto the inner surface of the sample container
  Dissolving the antibody (or the labelled antigen) in the saliva-sampling solution supplied
  Dissolving the sprayed-on antibody by rotation of the liquid in the device
  Incubating the mixture
    Here, the anti-drug antibodies react with the drugs (if present) present in the saliva, and they saturate a part of the antibody.
  Incubating with the inventive rotor
    The yet non-saturated antibodies, according to their specificity, bind to the antigens applied on the rotor (cylinder, carrier) in arrays.
  Washing
    Removing the antibodies not bound to the array and removing saliva liquids by exchange of liquids (wash solution) in the reaction space of the inventive device
  Scanning
    The antibodies bound may be detected via their fluorescence labelling. The light intensity collected is linearly proportional to the amount of fluorophores and, thus, proportional to the amount of antibodies bound. Thus, a quantitative statement on the amount of competitors (drugs) is possible.

Surprisingly, it has turned out that non-purified (i.e. non-centrifuged and filtrated) saliva in combination with the microarrays located on the rotor may be used directly. It is advantageous that, thus, there is no need for purification steps, whereby a mobile use (e.g. in case of traffic checks, directly in the hospital ward) is possible since mobile centrifuges with the G-number required (of more than 2000 g) are hardly realisable.

Due to the balanced intermixture (temperature, concentrations, disturbances) in the inventive device the variation of the measurement result within the device may be minimised (about 2 to 7%).

By providing raised parts and/or elevations preferably on the rotor, mucilaginous substances and suspended matter may be collected by the rotational movement in the same direction in the regions of the surface of the rotor and/or of the sample container which are not provided with detector molecules.

Providing a central channel allows for exchanging sample liquid with wash solution (e.g. by sucking-off via the lid), wherein the detector molecules do not become "dry" and the temperature does not suddenly change (solutions have substantially the same temperature as the liquid present in the device). Thus, conditions as constant as possible can also be achieved between the individual inventive devices, thus obtaining slight variations between the individual devices (below 10%).

Detection of nucleic acids (DNA, RNA) in a sample may be effected by means of a further method with the inventive device. After having been collected (e.g. blood), the sample is pre-treated and the nucleic acid is pre-purified. The detection is effected via fluorescence-intensity measurement of the array on the carrier (rotor). The signal originates from flourophores which are in adsorptive or also covalent contact with the immobilised molecules of the array of the rotor. Here, two signal-generating methods are used:

1. Nucleic-acid intercalating substances (Sybr Green, Boxto, ethidium bromide)
2. Fluorescence energy transfer (to quenching dyes and/or other fluorophores)

Both methods have in common that they require an enzymatic reaction to obtain a detectable measured variable.

In the first case of application this reaction will be the DNA-dependent DNA polymerase (preferably Taq polymerase). The procedure is generally termed solid phase PCR (polymerase chain reaction) and/or solid phase amplification. Here, the whole procedure of analysis is the following (example infection diagnostics; pathogen-specific DNA primer are spotted onto the surface of the rotor as array):

1. The sample (e.g. blood) is collected from the patient.
2. The DNA of the sample(s) is appropriately prepared.
3. A part of this preparation is used for root-cause diagnostics and filled into the inventive device together with the enzyme for the polymerase and other necessary reagents (e.g. puffer, etc.).
4. The sample is denaturated (94° C.), here, the double strands separate into DNA single strands.
5. Then, the sample is cooled down (annealing temperature 70° C.). Double strands form on each spot with the immobilised primers on the surface of the rotor (CIS-PCR).
6. The device is rotated at 72° C. and incubated: here, polymerisation (chain extension) of the primers occurs due to the hybridised DNA sample molecules.
7. The sample is again denaturated (94° C.), the double strands separate again.
8. During cooling the sample anew down to the annealing temperature (70° C.), double strands form with the primers extended by step 5 and 6 with adjacent (=same spot) second primers (differing from the first primer in that they have then reversed DNA sequence and, thus, comprise a sequence which is referred to as amplicon).
9. This double-strand formation is measured by the aid of a fluorescence measurement (e.g. FRET or CYBRgreen).
10. The steps 4 to 9 are cyclically repeated until an informative signal is to be expected.

The above representation of the analysing procedure makes clear that for converting a CIS-PCR array a spatially resolved measurement is required, on the one hand, and there must be the possibility to repeat this measurement as often as desired without changing the analysing conditions (e.g. by drying the solid phase), on the other hand. Moreover, the measuring system must be capable of changing the temperature in the samples according to an adjustable profile at any time. The inventive device is the only technology known to us which meets all these requirements and allows for the method known per se to be carried out for the first time safely.

Further methods which may be conducted in the prior art under static conditions may well be implemented with the inventive device. The inventive device is suitable for direct-reverse-transcriptase PRC on a solid carrier (e.g. U.S. Pat. No. 6,844,158), determination of DNA polymorphisms (e.g. DE 10 160 983), determination of DNA sequences by means of parallel amplification (e.g. EP 1 186 699), solid-phase PCR (e.g. JP 2001 299 346, U.S. Pat. No. 5,641,658, WO 93/09250, WO 69/26291), qualitative and quantitative determination of nucleic-acid molecules in a sample (e.g. WO 94/09156, WO 90/06042), solid-phase nucleic acid sequencing (e.g. WO 98/44152) and solid-phase primer extension (e.g. EP 0 370 694).

The analysis device in which the inventive device may be used to analyse the samples, may comprise several components, wherein particularly at least one rotation and detection device is necessary. Furthermore, the analysis device may include a light source (e.g. laser box), an incubation chamber, a liquid-exchange device (optionally coupled with a rotation device), several liquid reservoirs and a magazine. Thus, a typical analysis device may comprise the following components:

1. A laser box: location of the laser sources (up to 3 different types of lasers in parallel) or light sources which escape the box in a bundled and centred manner
2. An incubation chamber: location of temperature control, rotation, liquid exchange and measurement
3. A rotation and liquid-exchange device: serves for receiving the inventive device on the lid, provides for rotation, transport in the device, thus, also for positioning, liquid exchange (supply and discharge)
4. A detector: e.g. a CCD camera, alternatively also avalanche photo diodes (APD)
5. Liquid reservoirs: they are under controlled overpressure and negative pressure, whereby a supply and discharge of liquids is rendered possible in combination with item 3. and valves positioned there.
6. A magazine: location of the inventive device, which magazine may be managed by the device prior to and after the measurement, e.g. 8 pieces per each magazine.

The present invention will be explained in more detail by way of the following figures and examples, yet without being restricted thereto.

FIG. 3 shows a top view of the rotor.

FIG. 4 shows a cross-section of the rotor (section A-A of FIG. 3).

FIG. 12 shows the enlargement of detail B of FIG. 10.

FIG. 14 shows a spatial view of an inventive cartridge.

FIG. 21 shows a side view of an inventive device including a sample container, rotor and lid, wherein the interrupted lines are edges which are not visible from the outside.

FIG. 22 shows a cross-section of an inventive device including a sample container, rotor and lid (section A-A of FIG. 21).

Figure 33:
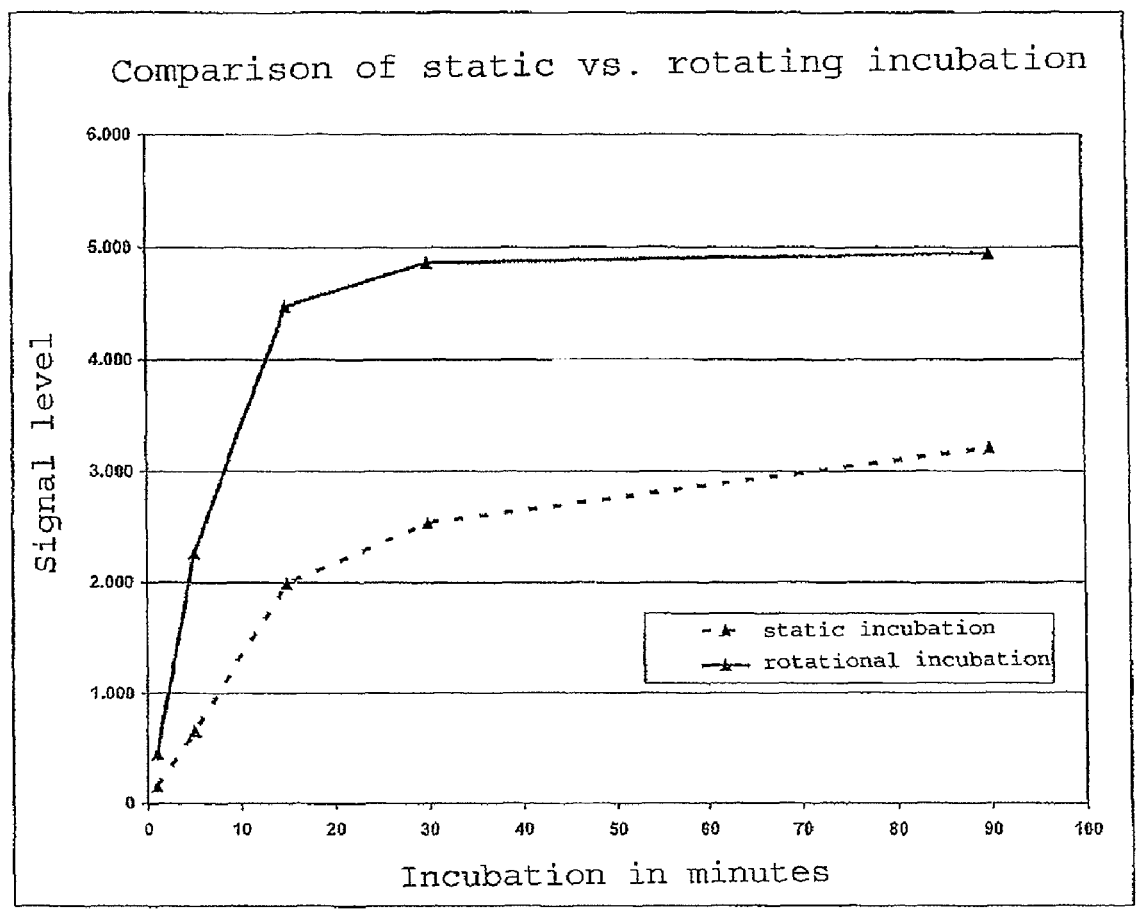
Figure 34:
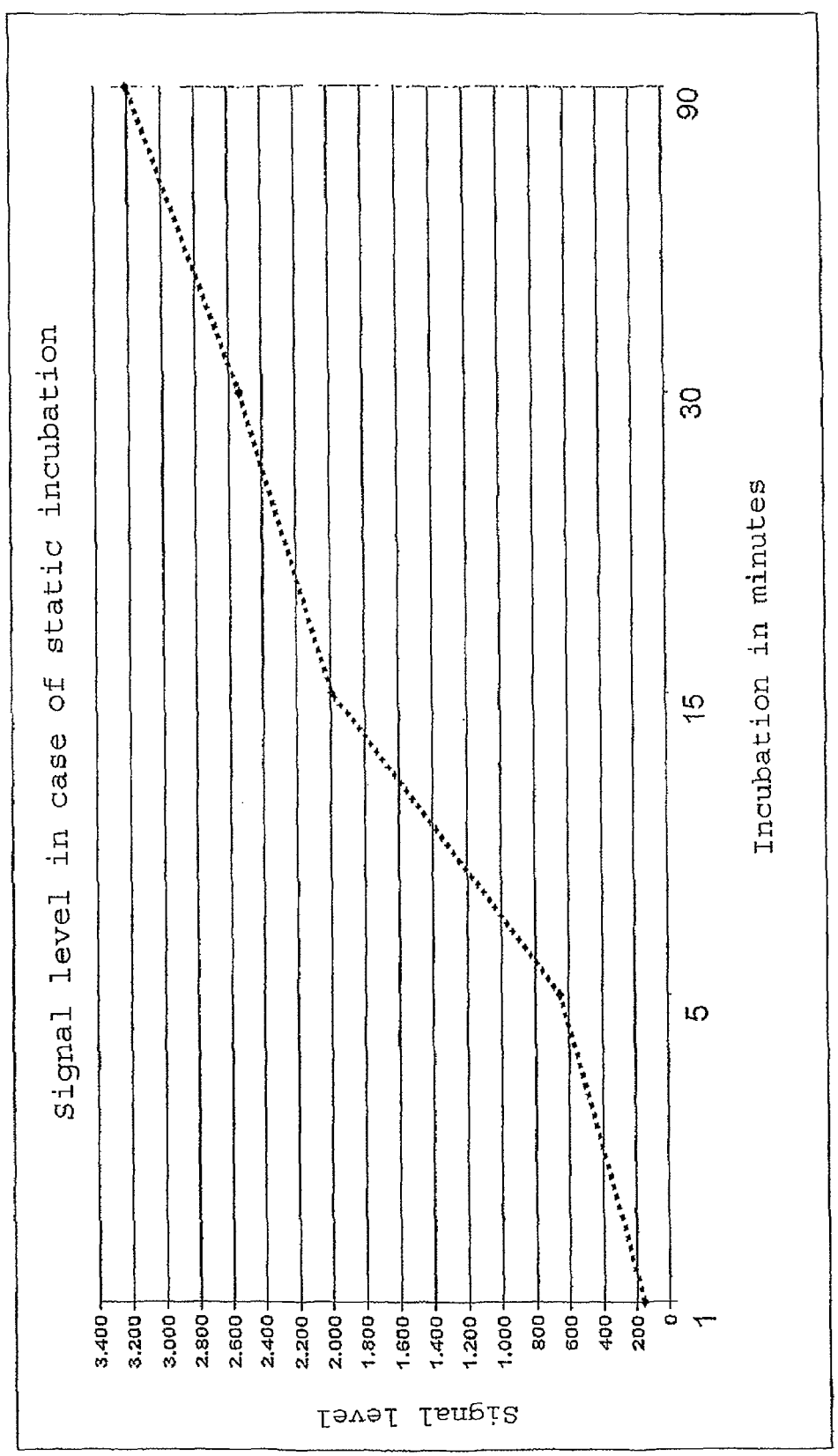

FIGS. 33 and 34 show the maximal signal level of measurements done with the inventive device, wherein the surface of the rotor had been spotted with antibodies (specifically against murine antibodies) and had been incubated with monoclonal murine antibodies (fluorescence-labelled with Dylight 547). After incubation, the rotors were washed with PBS 0.5% Tween 20 and scanned. The series of measurements corresponds to the individual measurements with different incubation time. The maximum reached after about 30 min becomes apparent in the case of the series of measurements with rotating incubation. Not even after 90 min, i.e. after the threefold incubation time, does the static incubation reach the signal level nor a stagnation of the signal rise. In case of reproduceable measurements, in particular with individual measurements as they are presently common, a balance (stagnating, decreasing signal level) needs to be reached.

Figure 35:
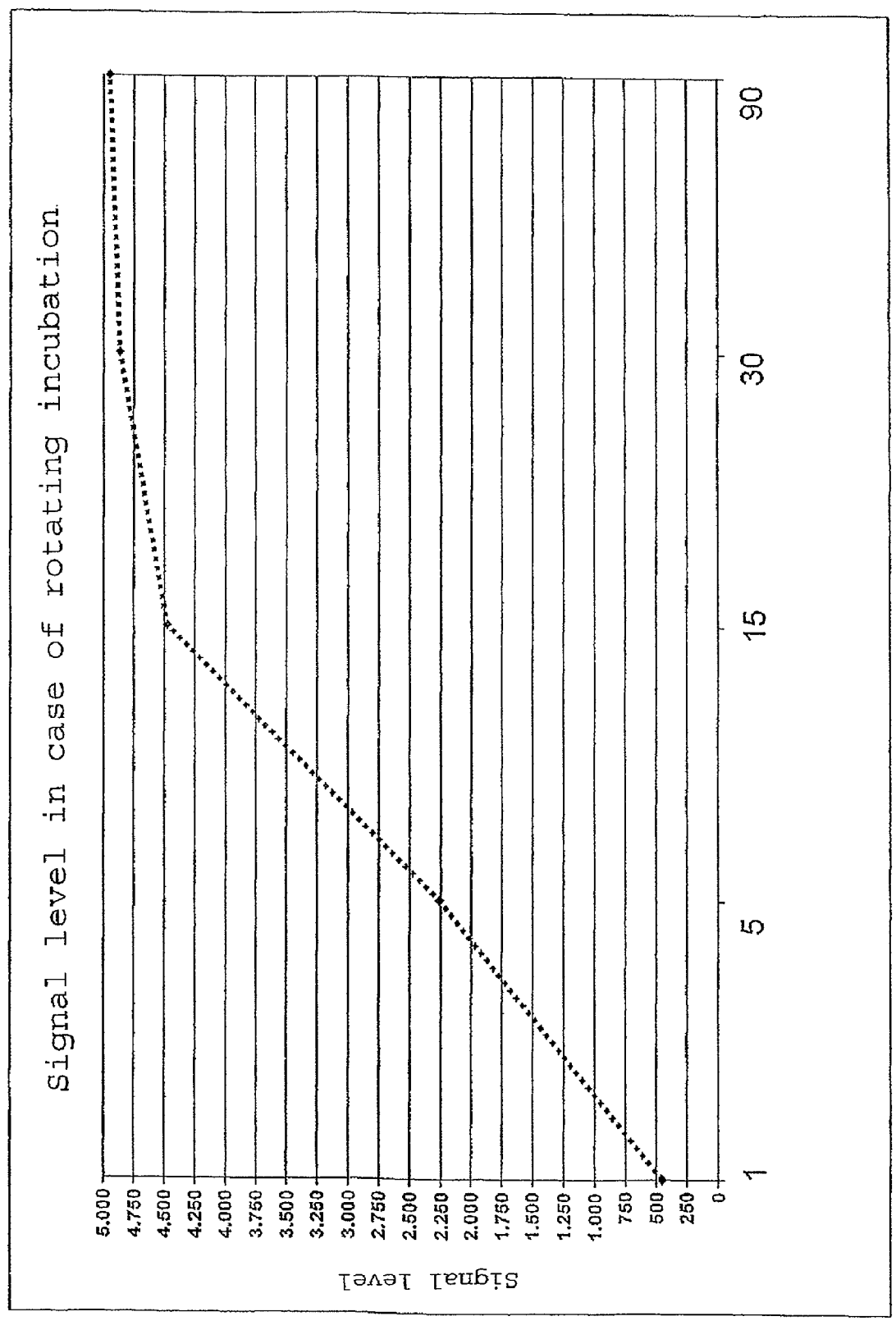

FIG. 35 shows the dependence of the signal level from the incubation time in case of a rotating incubation.

Figure 36:
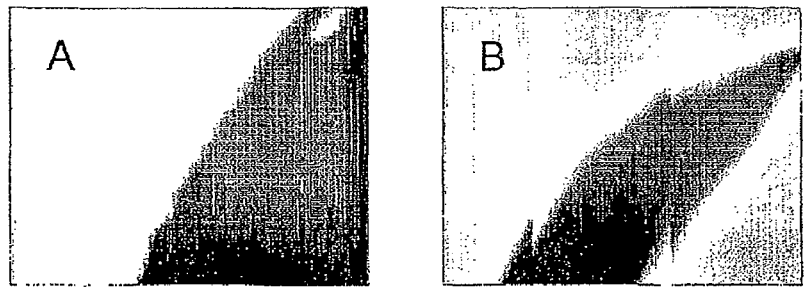

FIG. 36 shows the reception of a labelled spot present on the rotor during rotating centred (A) and non-centred (B) mounting of the rotor.

Figure 37:
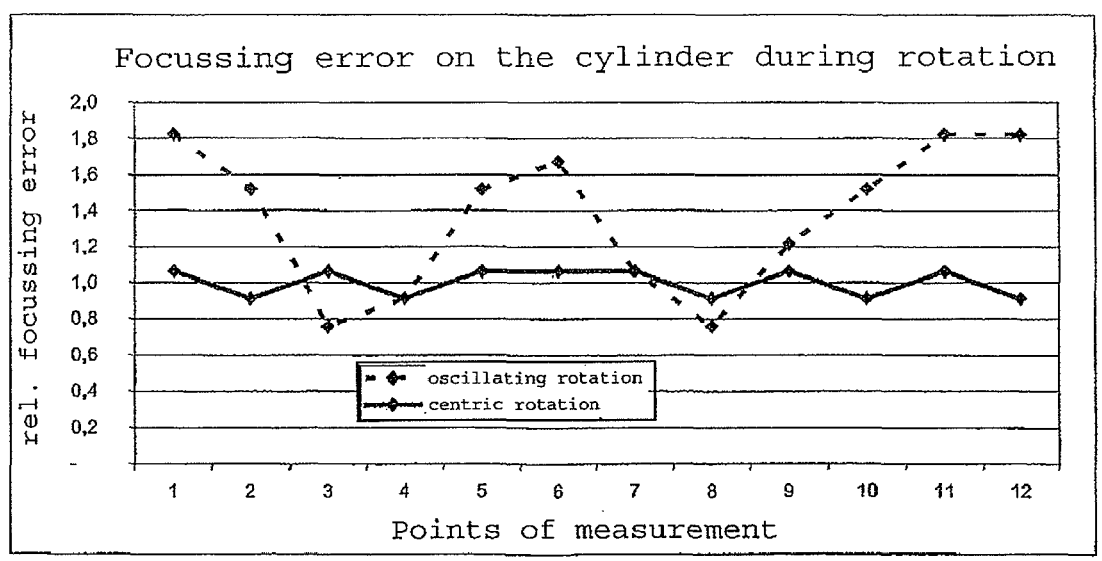

FIG. 37 shows the relative focussing errors in case of a rotating incubation with the inventive device in comparison with a device which has no means for centred mounting.

Figure 38:
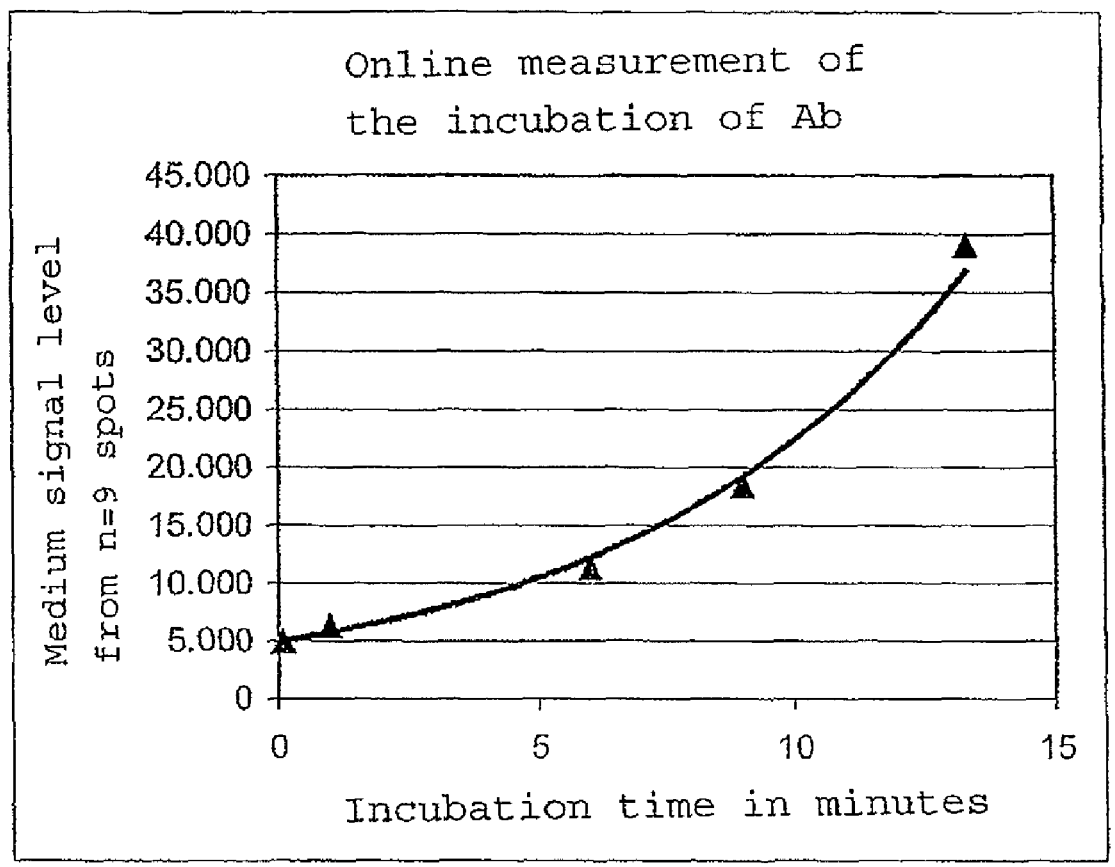

FIG. 38 shows the reception of the signal as a function of time (bond kinetics).

Figure 1:
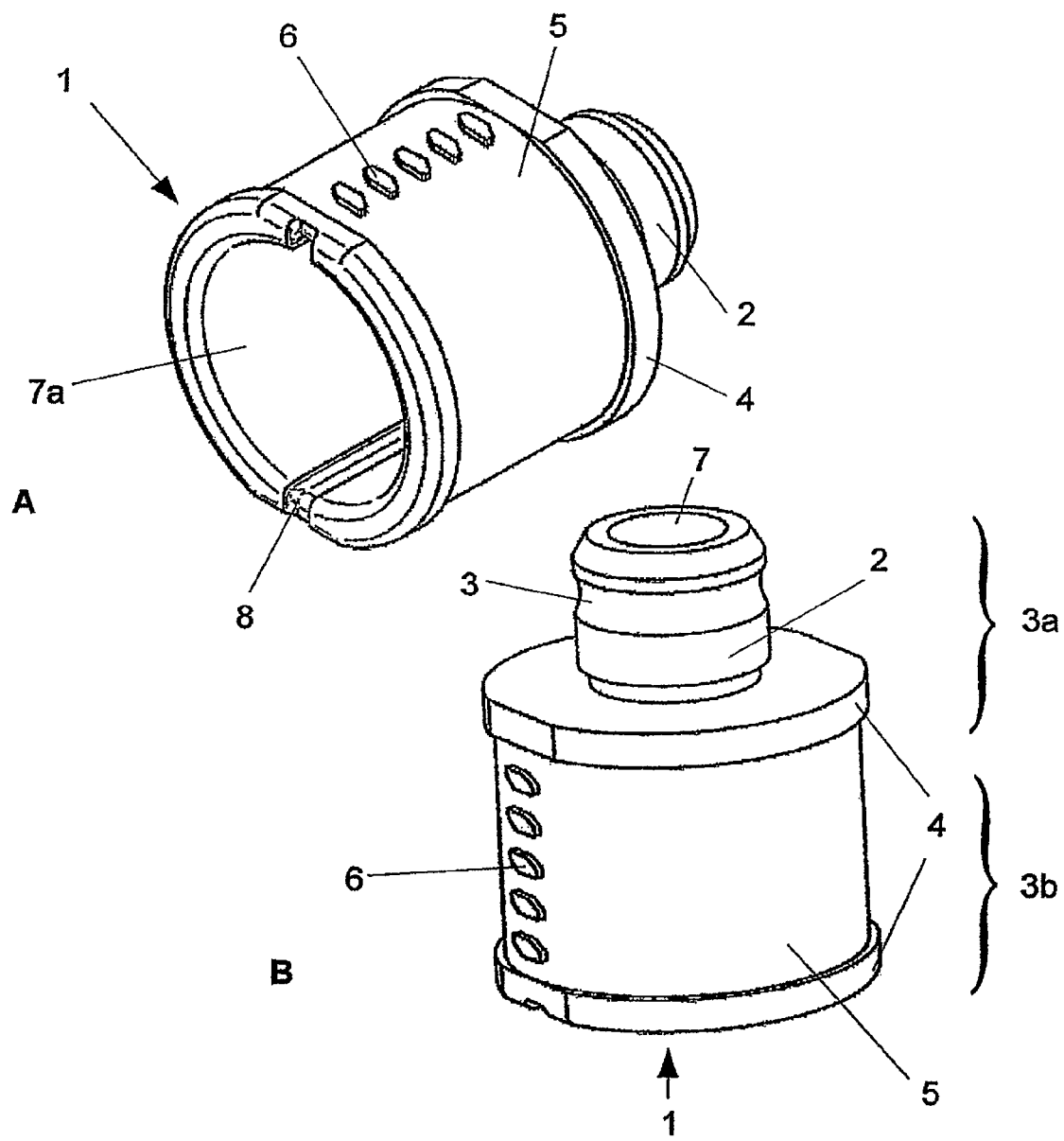
FIGS. 1A and 1B show two spatial views of an inventive rotor.

In FIGS. 1A and 1B an inventive cylindrical rotor 1 is shown which has a fastening means 2 comprising a radial recess 3 for fixing a lid. In the upper 3a and lower 3b region, the rotor 1 has an outward-directed radial projection 4. On the outer surface 5 of the rotor 1, elevations 6 are provided which serve for better intermixture of the sample liquid present between the sample container and the rotor 1. Furthermore, the rotor 1 comprises a flow channel 7 which has a smaller diameter in the upper region 3a of the rotor 1 in the fastening means 2b than in the lower region 3b of the rotor 1. Two depressions 8 are provided in the flow channel 7 which extend along the latter and serve for transporting a liquid along the flow channel 7.

Figure 2:
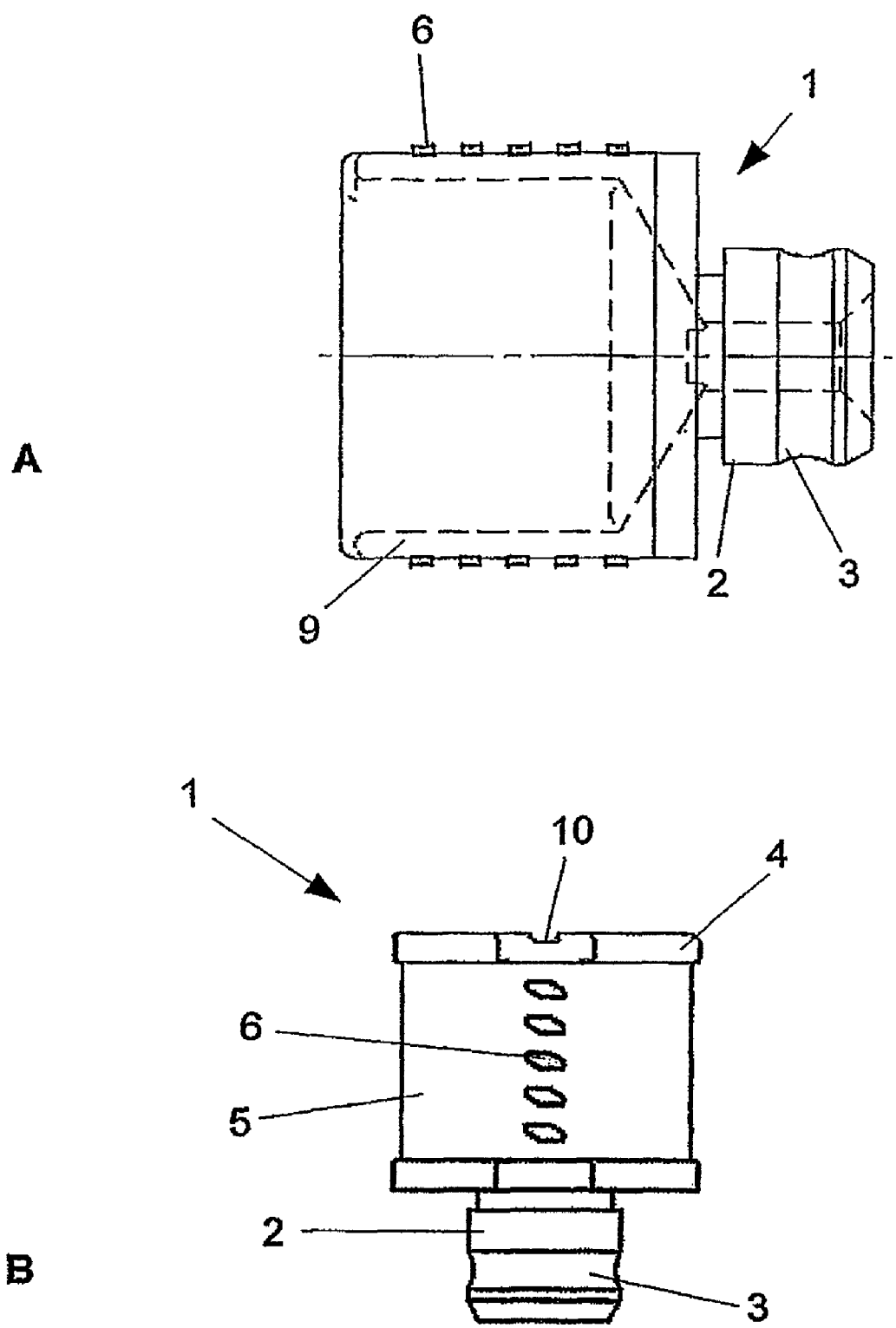
FIGS. 2A and 2B show a side view of the rotor.

FIGS. 2A and 2B show a further side view of the rotor 1 (as in FIGS. 1A and 1B), wherein in FIG. 2 the inner delimitation 9 of the flow channel 7 is illustrated with an interrupted line. In the lower region 3b of the rotor 1, a recess 10 is provided which allows for a liquid passage from the flow channel 7 into the sample space (radial gap between the rotor 1 and the sample container 11) when the sample container 11 has been fully introduced into the rotor 1.

FIG. 3 is a top view of the rotor 1, wherein the inner delimitation 9 of the flow channel 7 in the rotor 1 is shown by way of interrupted lines.

In FIG. 4 a cross-section (section A-A, FIG. 3) of the rotor 1 is shown. The flow channel 7 of the rotor 1 has a larger diameter in the lower region 3b than in the upper region 3a. Moreover, the flow channel 7 is cylindrical in the lower region 3b and frustoconical in the region of the reducing diameter. In the fastening means the flow channel is again cylindrical.

Figure 5:
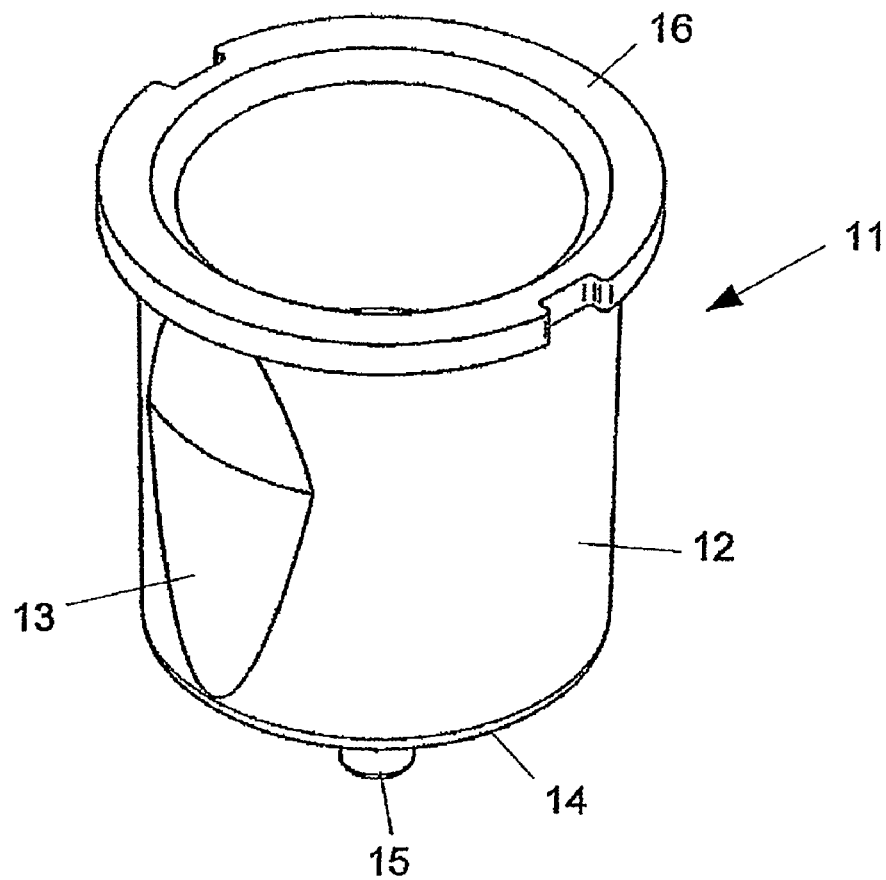
FIG. 5 shows a spatial view of a sample container according to the present invention.

FIG. 5 shows the spatial illustration of a sample container 11 which is designed for receiving the rotor 1. The sample container 11 has a transparent inspection window 13 on the lateral delimitation 12, through which the signals generated in the inventive device may pass in a substantially unhindered manner. The transparent inspection window 13 may be adapted according to the measuring system used and may, e.g. have a curvature. At the bottom 14 of the sample container two elevations 15 (e.g. in the form of nubs) are provided which are suited to radially fix the sample container 11 when they have been introduced into an appropriate depression of a planar surface. The sample container 11 comprises a radial projection 16 at its opening for receiving the rotor 1.

Figure 6:
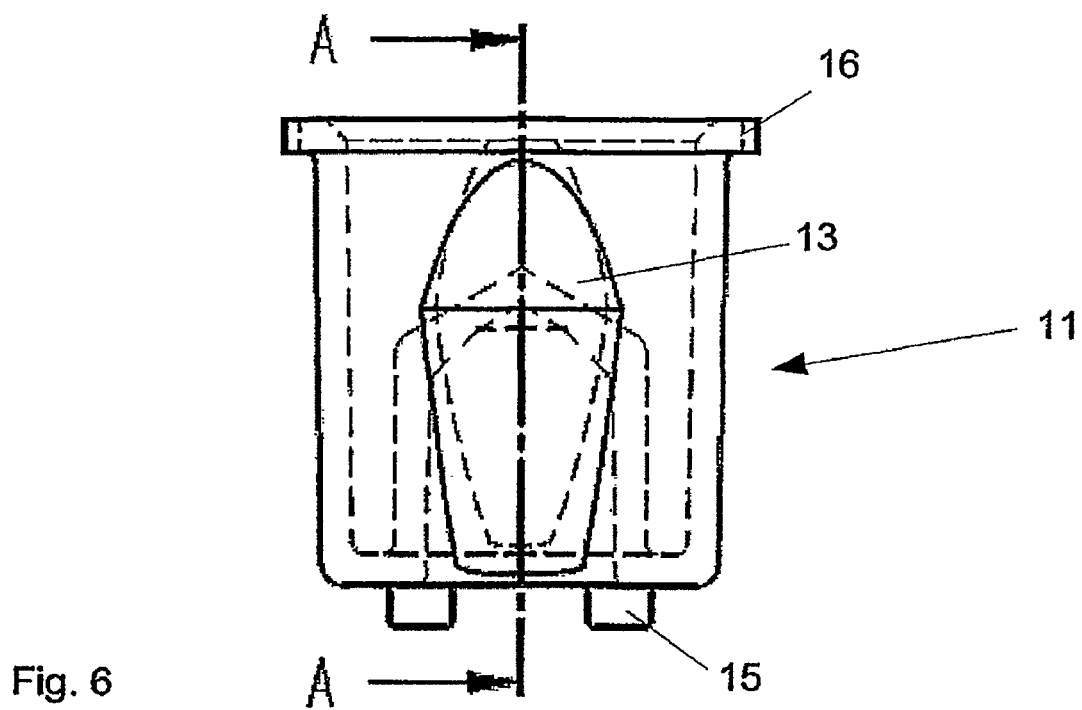
FIG. 6 shows a side view of the sample container.

FIG. 6 shows a side view of the sample container 11 (cf. FIG. 5). The interrupted lines indicate elements in the interior of the sample container which are illustrated in more detail in FIG. 7.

Figure 7:
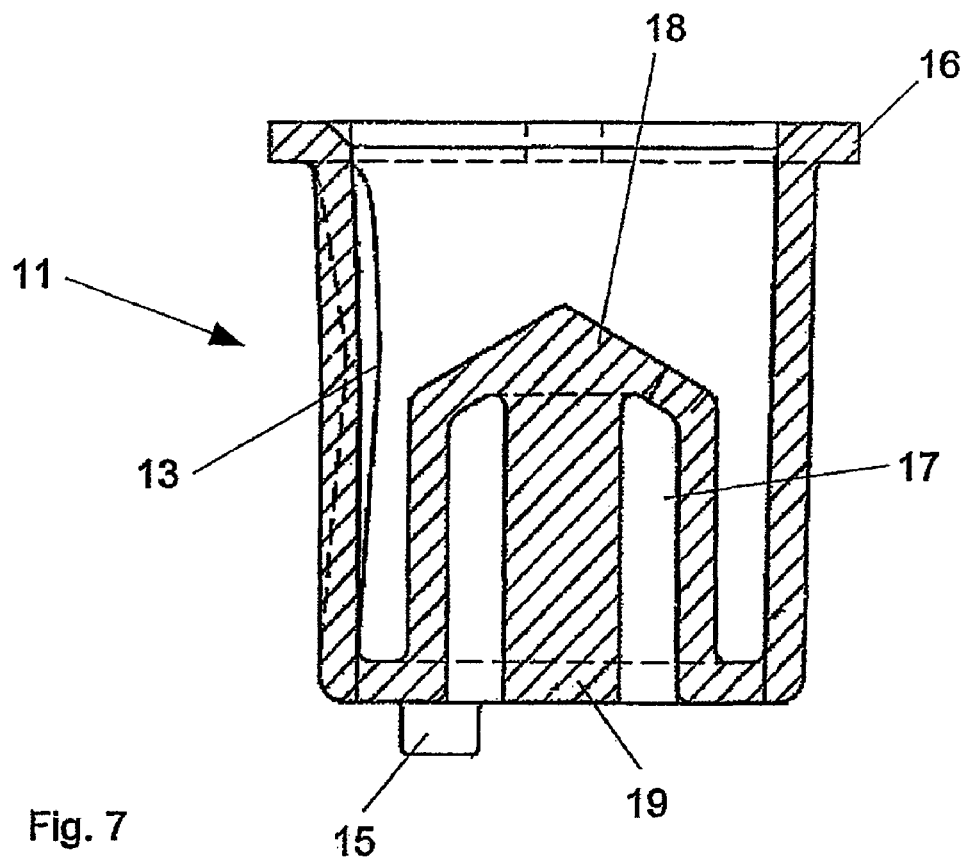
FIG. 7 shows a cross-section of the sample container (section A-A of FIG. 6).

In FIG. 7 the cross-section (section A-A) of the sample container 11 is shown. In the interior of the sample container 11, a cylindrical dent 17 with a conical end portion 18 is provided which is shaped for mounting the inventive rotor 1 radially movably. On the outer side of the sample container 11, in the dent 17, a cylindrical longitudinal body 19 is provided which may serve for positioning the sample container 11. Furthermore, a cooling and/or heating device may be introduced into the dent 17.

Figure 8:
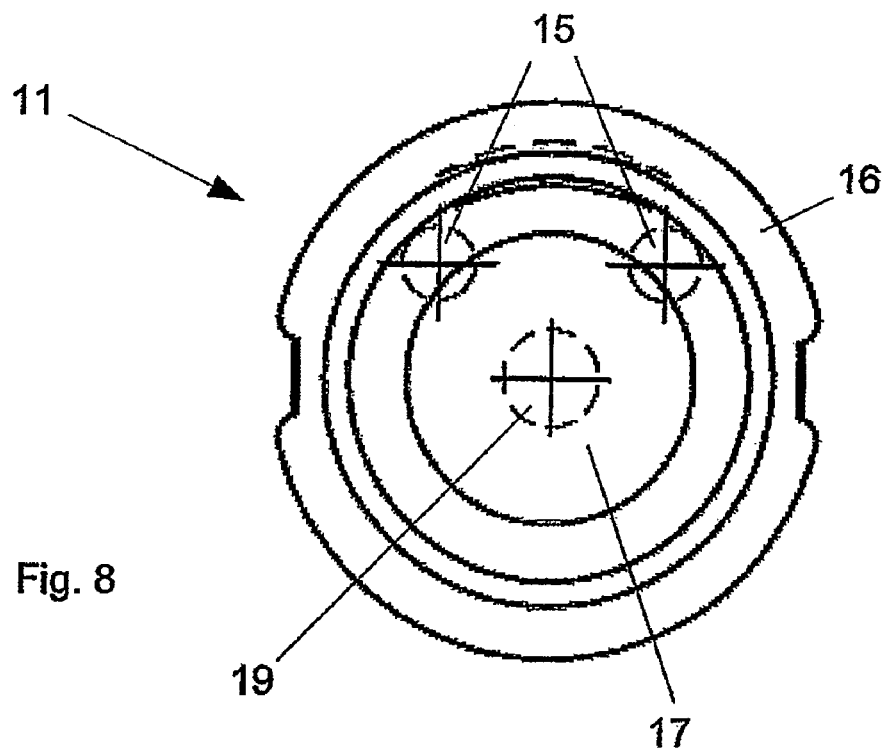
FIG. 8 shows a bottom view of the sample container.

FIG. 8 shows a bottom view of the sample container 11.

Figure 9:
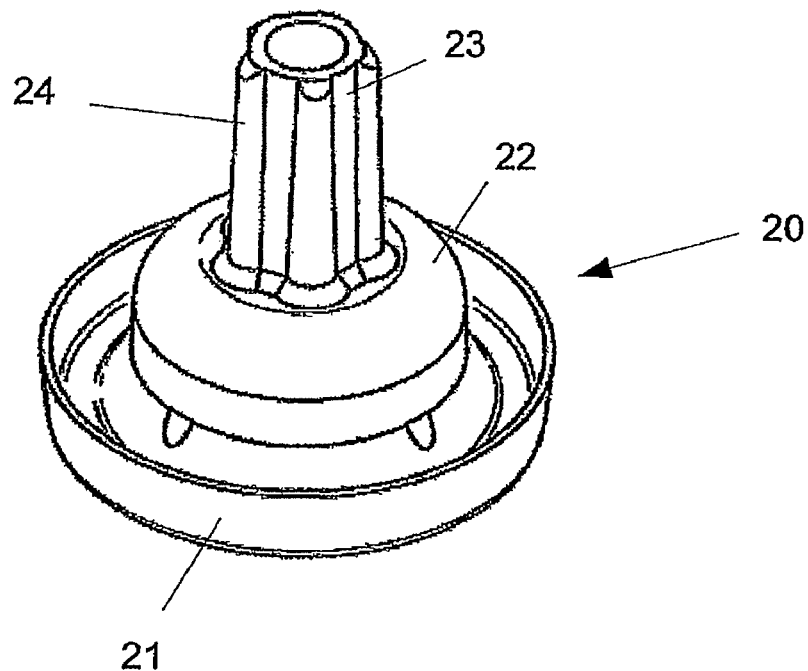
FIG. 9 shows a spatial view of an inventive lid.

In FIG. 9 an inventive lid 20 is shown which may be fixed to the rotor 1, in particular to its fastening means 2 (cf. FIGS. 2A and 2B). The lid 20 comprises a sealing lip 21 which serves for sealing the interior of the sample container so that it is liquid-proof and gas-proof. Furthermore, on the lid, a dent 22 is provided which comprises an opening and serves for both receiving the fastening means 2 of the rotor 1. On the dent 22, a cylindrical hollow body 23 is provided which may be used for introducing liquids into the sample container 11 and may serve for transferring a torque of a torque-generating device to the rotor 1. On the cylindrical hollow body 23, axially extending elevations 24 may be provided which improve the grip of the hollow body 23.

Figure 10:
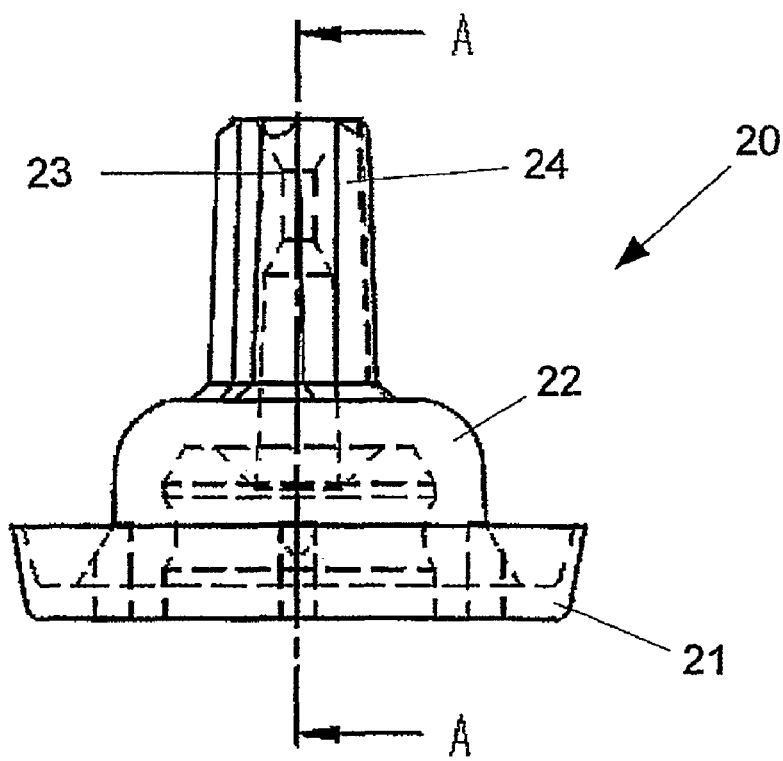
FIG. 10 shows a side view of the lid.
Figure 11:
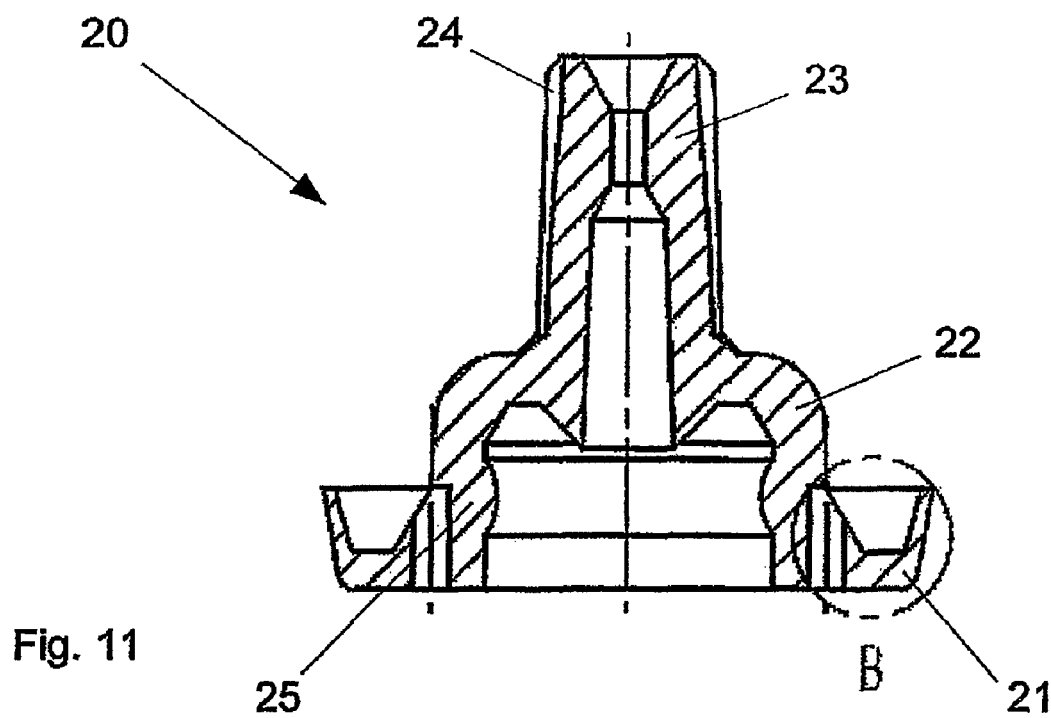
FIG. 11 shows a cross-section of the lid (section A-A of FIG. 10).
Figure 15:
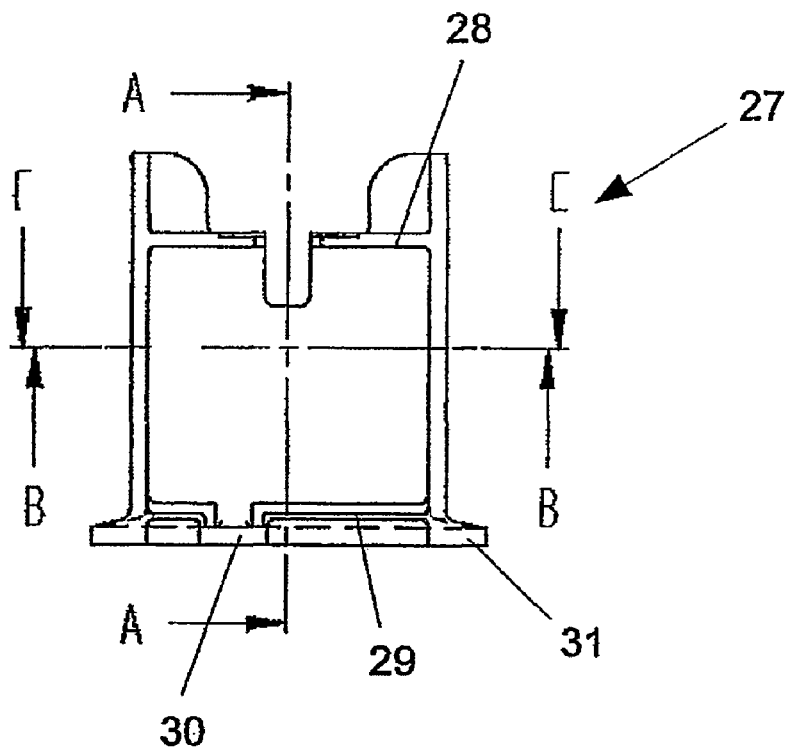
FIG. 15 shows a side view of the cartridge.
Figure 16:
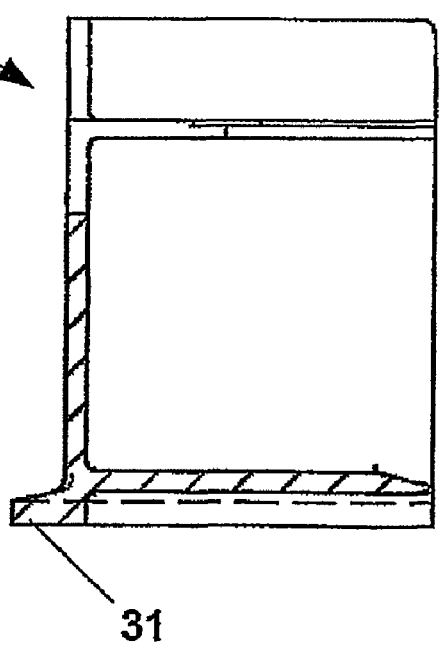
FIG. 16 shows a cross-section of the cartridge (section A-A of FIG. 15).
Figure 17:
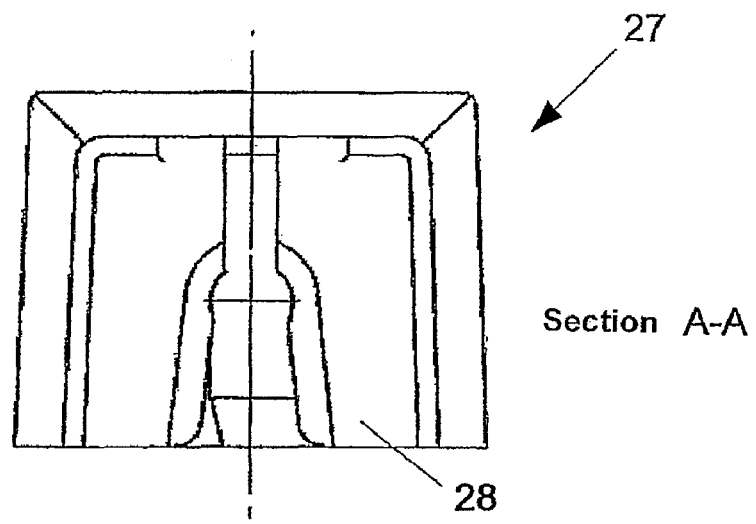
FIG. 17 shows a cross-section of the cartridge (section B-B of FIG. 15).
Figure 18:
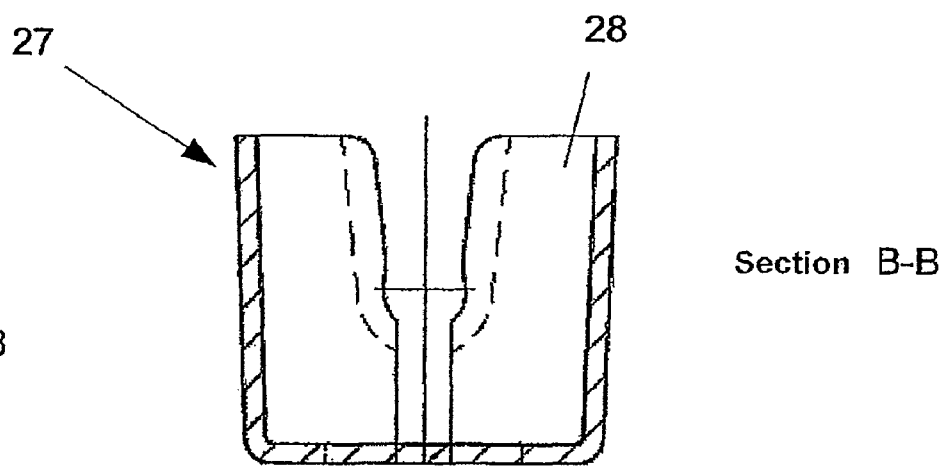
FIG. 18 shows a cross-section of the cartridge (section C-C of FIG. 15).
Figure 19:
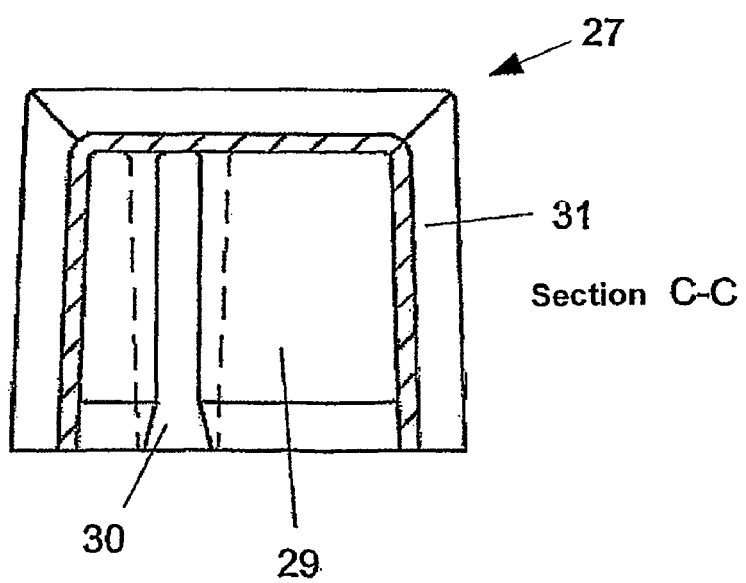
FIG. 19 shows a top view of the cartridge.

FIG. 10 shows a side view of the lid 20 whose cross-section is illustrated in FIG. 11. In the dent 22, a radial projection 25 is provided which may snap-in in the recess 3 of the fastening means 2 of the rotor 1. If a winding is provided instead of a recess 3, a winding is also to be arranged in the dent 22 in order to allow for fixing of the lid 20 to the rotor 1.

The detail B of FIG. 11 which comprises a sealing lip 21 is illustrated in FIG. 12 in an enlarged way. Directly next to the sealing lip 21, the lid 20 has at least one opening 26, through which either escaping gas or, in the case of a flow-through cell, escaping liquid may be removed from the sample container.

Figure 13:
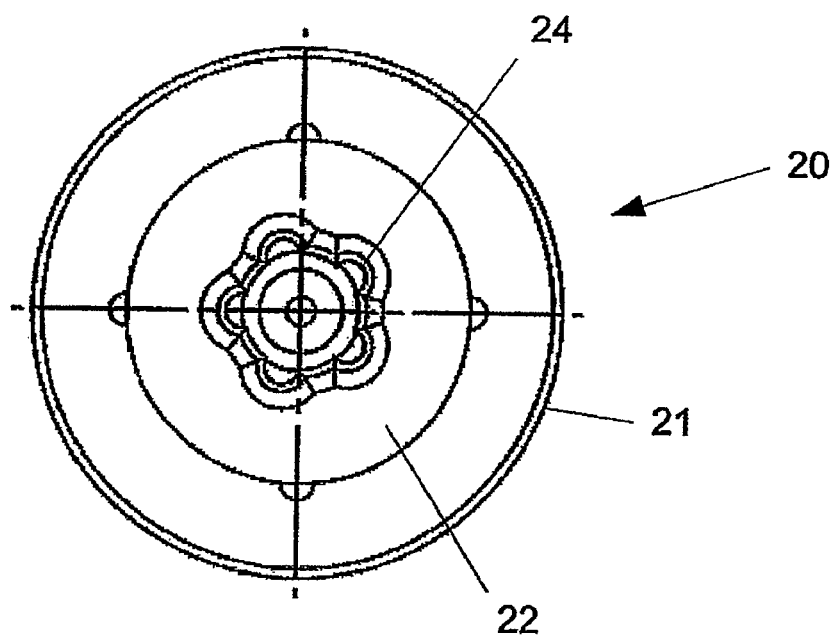
FIG. 13 shows a top view of the lid.

FIG. 13 is a top view of the lid 20.

FIG. 14 is a spatial view of the inventive cartridge 27 which is designed for receiving the inventive device including the rotor 1, sample container 11 and the lid 20. The cartridge has a horizontal plate 28 (lateral delimitation) which is provided with a slot that covers the entire depth and is designed to receive or mount radially movably the upper region 3a of the rotor 1 or the means 23 for transferring a torque to the rotor provided on the lid 20. In the bottom 29 of the cartridge, there is a guiding groove (recess) 30 which is substantially complementary to the elevations 15 present on the sample container 11 and prevents radial twisting of the sample container 11 when the device has been inserted. Since the rotor 1 is fixed in its position relative to the sample container 11 by means of the plate, lowering of the rotor 1 is prevented and a pre-incubation room is defined. The horizontal plate 28 is configured such that the pressure, which has to be applied by attaching the lid 20 manually or later automatically, is absorbed. Furthermore, on the bottom 29 of the cartridge an outward-directed projection 31 is provided which serves for stabilising the cartridge 27 on a bearing surface.

FIGS. 15 to 19 show different cross-sectional views of the cartridge 27.

Figure 20:
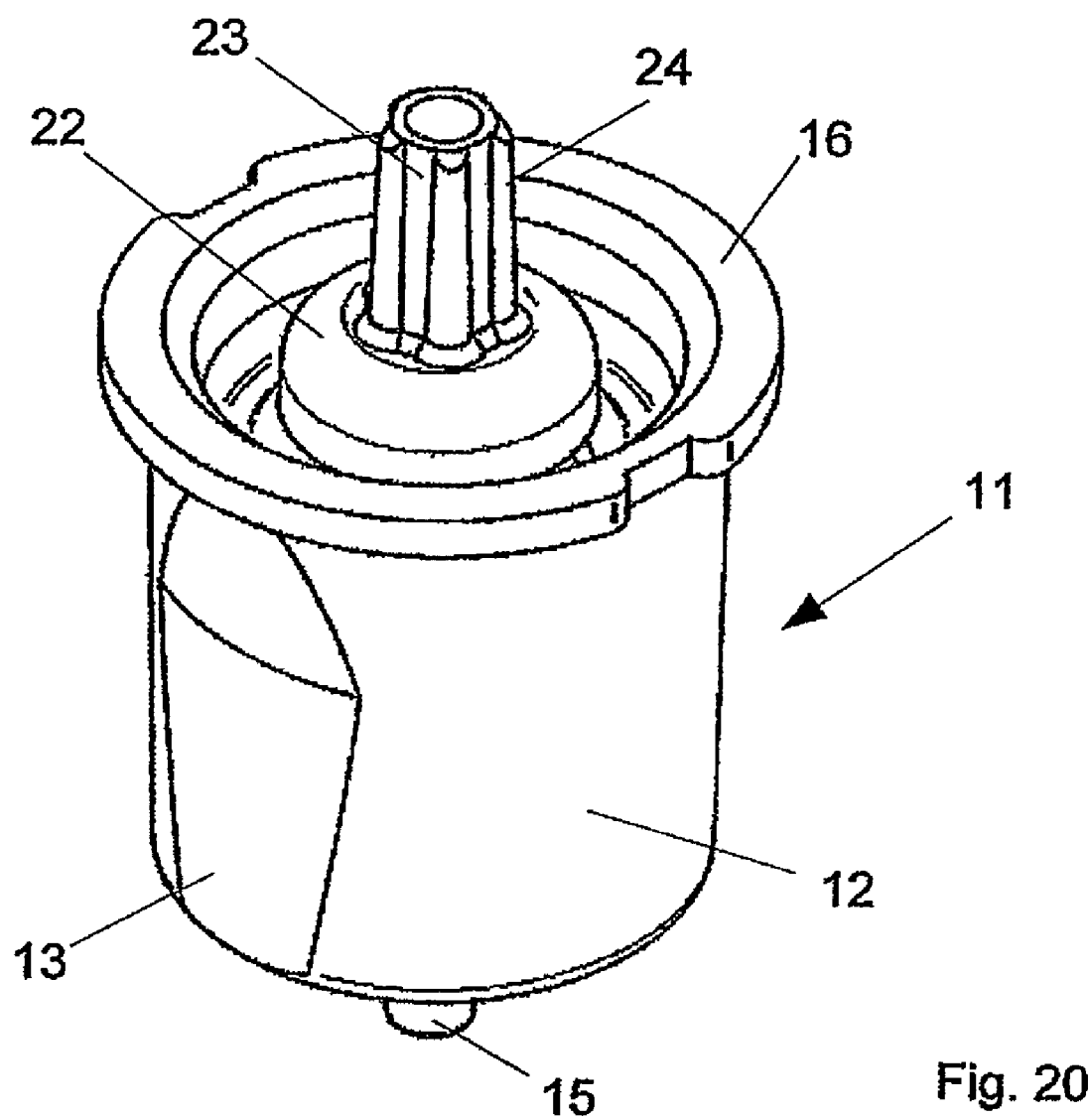
FIG. 20 shows a spatial view of an inventive device including a sample container, rotor and lid.

FIG. 20 shows the spatial view of an inventive device including a rotor 1, a lid 20 and a sample container 11. In this figure, the rotor 1 is provided fully in the sample container 11 (so-called "measuring position"). In order to be able to conduct a measurement by the aid of the inventive device, the rotor 1 has to be in this position during measurement.

FIG. 21 shows a side view of the inventive device, wherein the edges which are not visible from the outside are illustrated by interrupted lines.

FIG. 22 shows a cross-section of the inventive device. The sealing lip 21 of the lid 20 presses against the inner wall of the sample container 11 when in "measuring and analysing position" and, thus, forms a closed measuring space which allows for supply and discharge of liquids and/or gases (e.g. sample liquid, buffer, detection liquid, wash liquid), optionally through one or several openings, e.g. in the lid 20, whereby the inventive device may create a flow-through cell. A radial annular gap 32 is provided between the inner wall of the sample container 11 and the outer wall of the rotor 1.

Figures 23, 24:
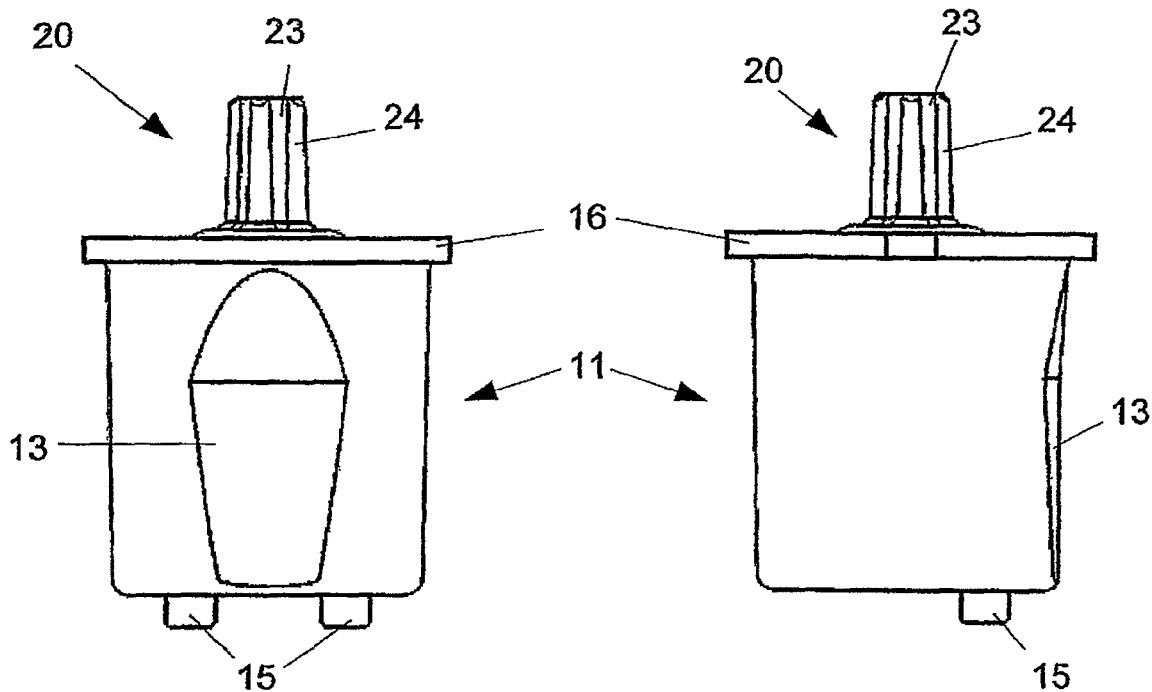
FIG. 23 shows a side view of an inventive device including a sample container, rotor and lid.
FIG. 24 shows a further side view of an inventive device including a sample container, rotor and lid.

In FIGS. 23 and 24 further side views of the inventive device are shown.

Figure 25:
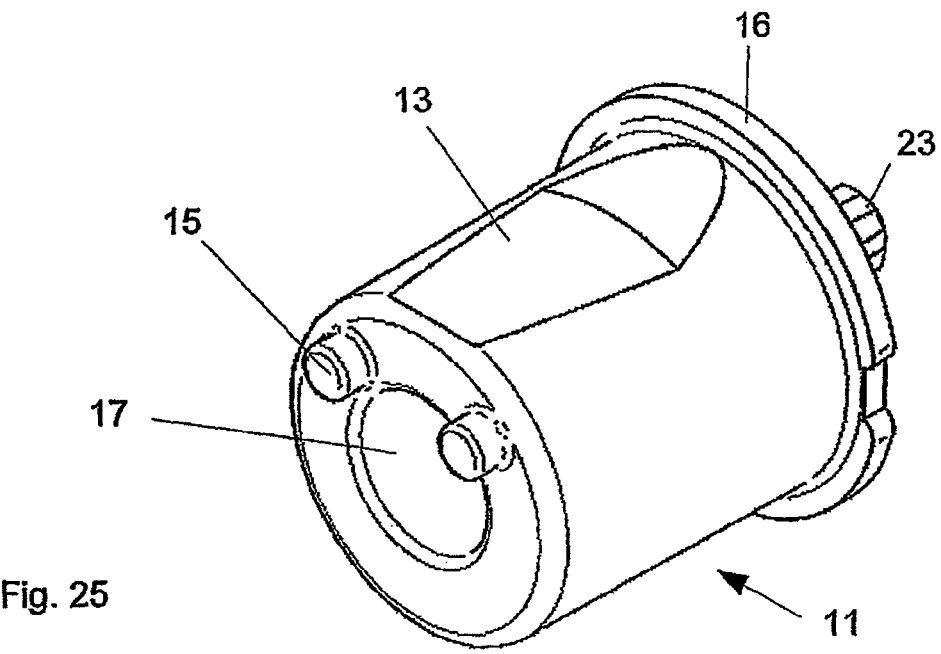
FIG. 25 shows a spatial view of an inventive device including a sample container, rotor and lid.

FIG. 25 is a further spatial view of the inventive device. Here, the dent 17 of the sample container 11 is visible which may optionally at least partly serve as bearing surface for the rotor 1. The elevations 15 at the bottom of the sample container serve for radial fixing of the sample container 11 in a cartridge 27.

Figure 26:
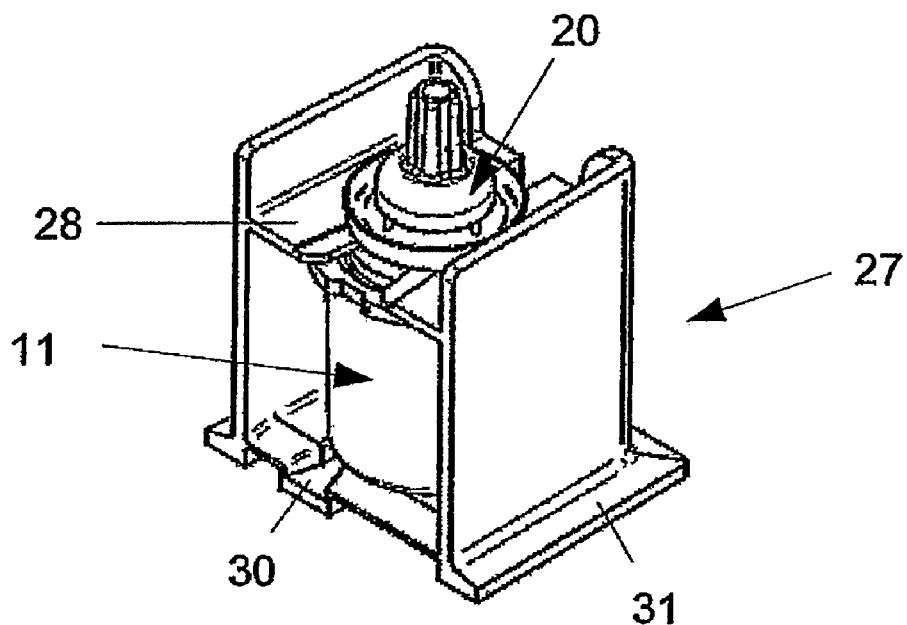
FIG. 26 shows a spatial view of an inventive device including a sample container, rotor and lid in an inventive cartridge.
Figure 27:
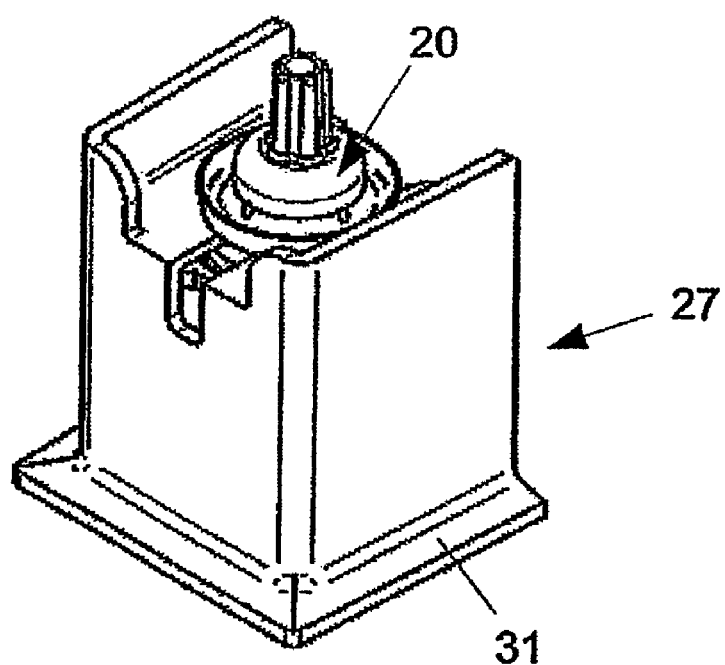
FIG. 27 shows a further spatial view of an inventive device including a sample container, rotor and lid in an inventive cartridge.
Figure 28:
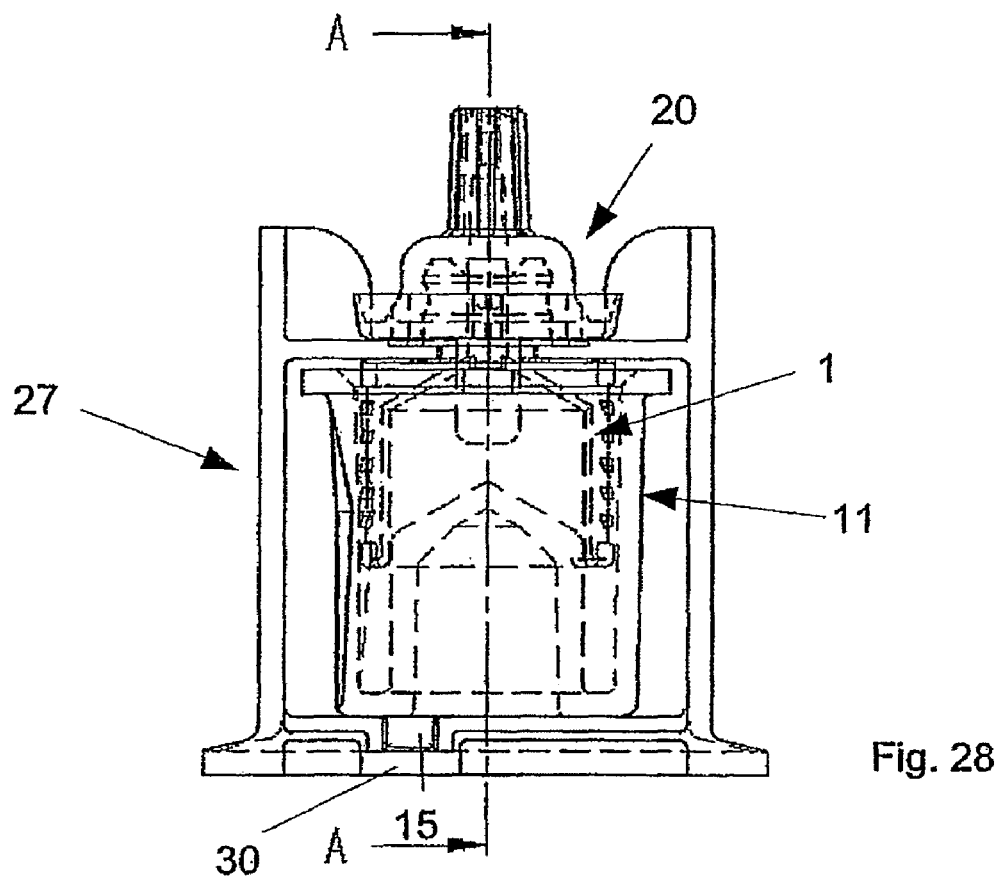
FIG. 28 shows a side view of an inventive device including a sample container, rotor and lid in an inventive cartridge, wherein the interrupted lines are edges which are not visible from the outside.
Figure 29:
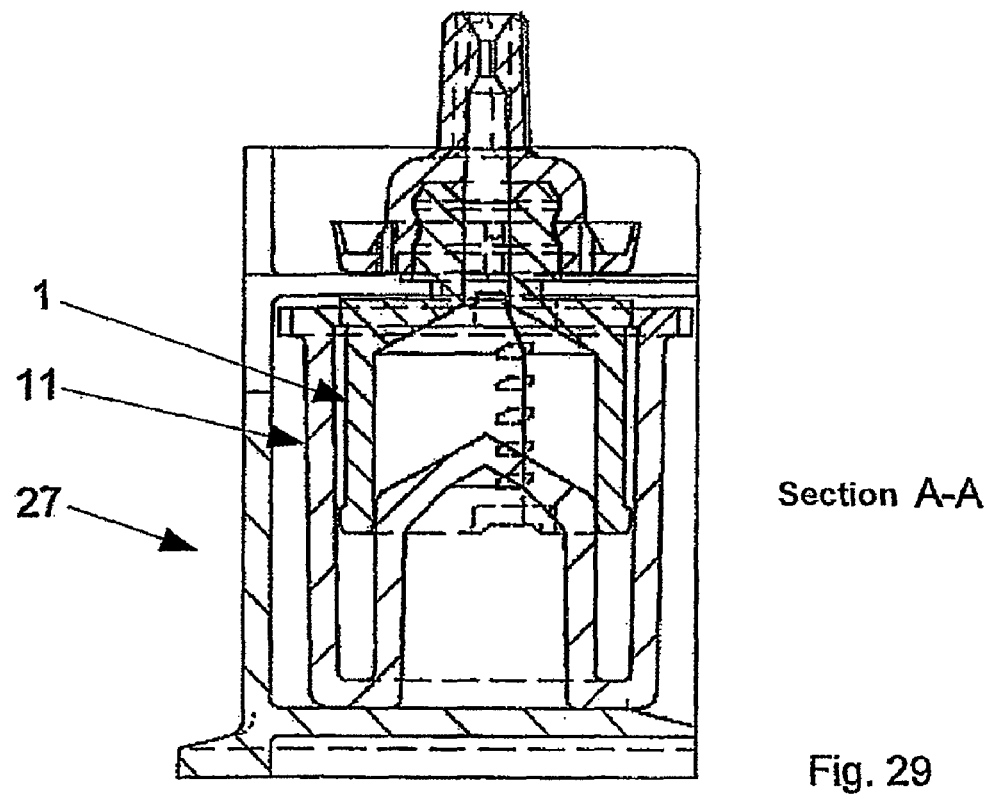
FIG. 29 shows a cross-section of an inventive device including a sample container, rotor and lid in an inventive cartridge (section A-A of FIG. 28).
Figure 30:
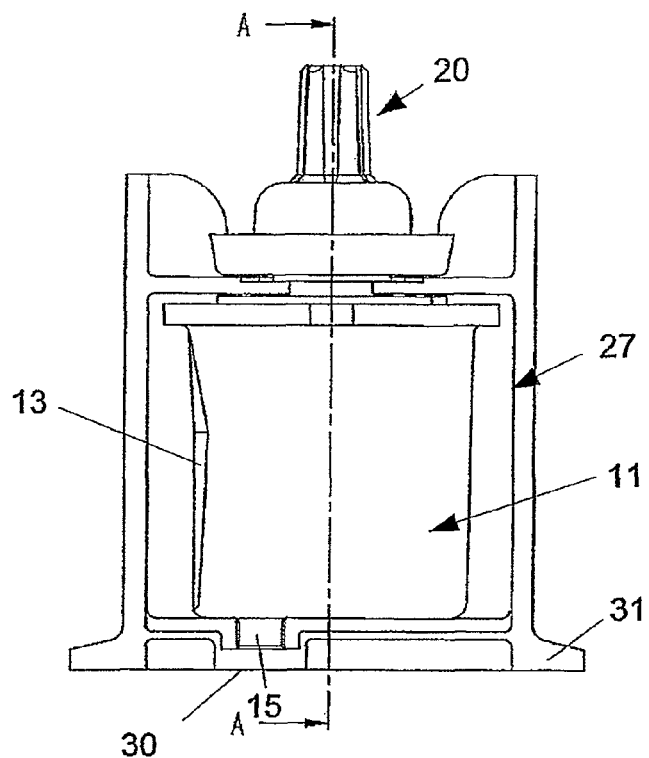
FIG. 30 shows a further side view of an inventive device including a sample container, rotor and lid in an inventive cartridge.
Figure 31:
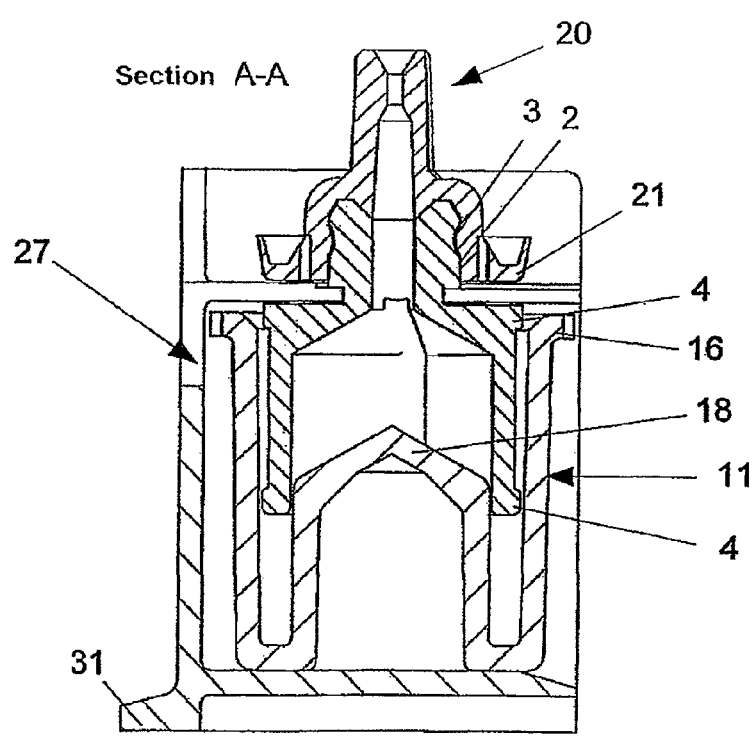
FIG. 31 shows a cross-section of an inventive device including a sample container, rotor and lid in an inventive cartridge (section A-A of FIG. 30).

FIGS. 26 and 27 are a spatial illustration of the inventive device in a cartridge 27. Here, the elevations 15 at the bottom of the sample container are located in the guiding groove 30 in the bottom 29 of the cartridge. The position which the inventive device has in the cartridge 27 may be referred to a "mounting position" since the rotor 1, in this position, is not fully located in the sample container and, thus, no annular gap 32 may be formed which would be necessary for measurement. Furthermore, in this position, no sufficient torque may be applied onto the rotor 1 due to the friction between the upper region 3a of the rotor 1, the fastening means 2 and/or the lid 20 with the slot of the horizontal plate 28 and/or the horizontal plate 28 itself which serves for fixing the inventive device in the cartridge 27. The slot of the horizontal plate 28 serves for receiving the fastening means 2 of the rotor 1. Thus, the horizontal plate 28 is surrounded, on one side, by the lid and, on the other side, by the rotor 1.

In FIGS. 28 to 31, this "mounting position" is again dealt with in more detail.

EXAMPLE 1

Figure 32:
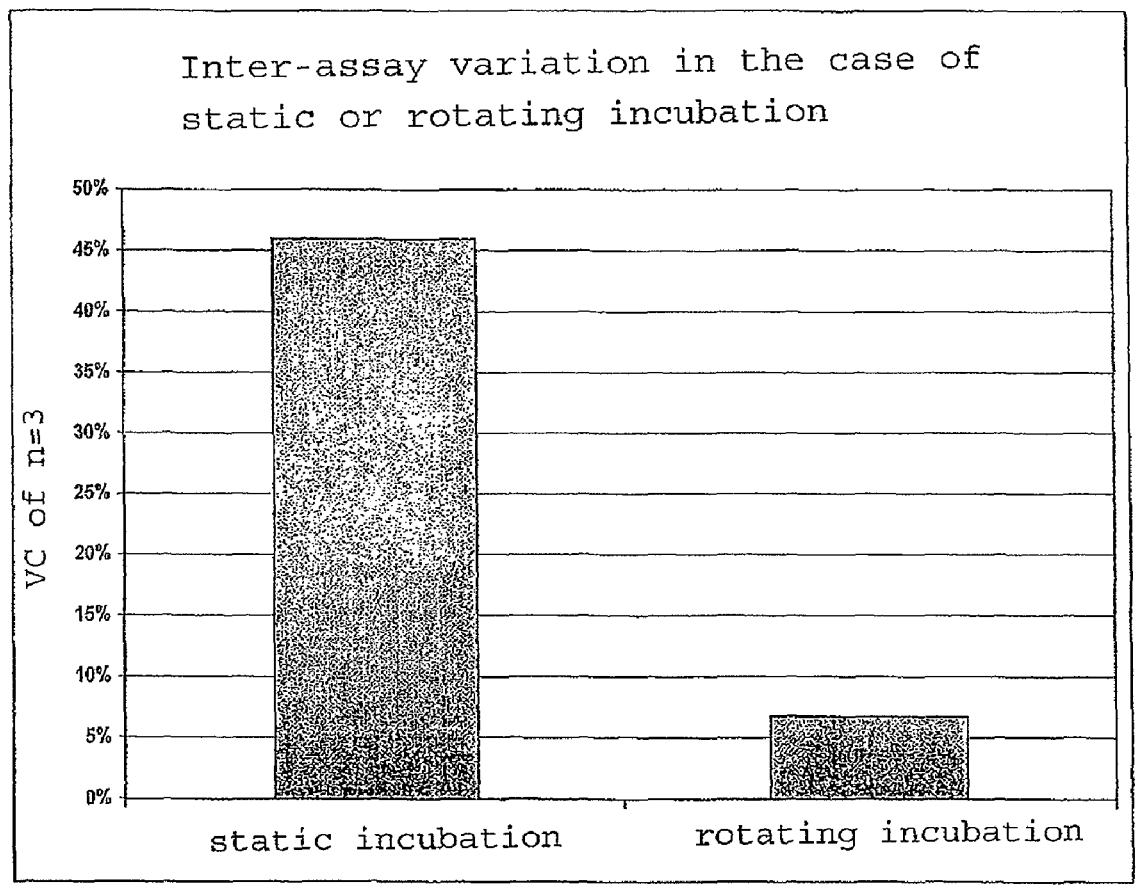
FIG. 32 shows the variation coefficients of measurements done with the inventive device, wherein the surface of the rotor had been spotted with antibodies (specifically against murine antibodies) and had been incubated with monoclonal murine anti-bodies (fluorescence-labelled with Dylight 547). After incubation, the rotors were washed with PBS 0.5% Tween 20 and scanned.

Variation Coefficient of Measurements Done by the Inventive Device in Case of Static and Rotating Incubation In order to show the positive effect of the rotating anti-body incubation of the inventive device ("Hybcell") on the inter-variation coefficient, i.e. on the variation coefficient between the different devices, three AuPd-coated and activated (DSP: dithiobis(succinimidylpropionate) or also Lomant's reagent) devices were incubated with fluorescence-labelled markers twice either in a static or rotating manner. Here, interactions with the specific antigen (morphine) occur, which antigen has been immobilised on the jacket surface of a cylinder in the form of round spots. As can be seen from FIG. 32 and Table 1, in case of rotating incubation, the intervariation coefficient is reduced by the factor 9, constituting a very clear improvement in comparison with static incubation.

TABLE 1

Scanning settings were 0.9 7 300. The devices were labelled with 1 µl of antibody (1 mg/ml) for 5 min, incubated with Dylight 547 nm in a rotating or static manner, evaluation was done with a diameter of 200 µm.

| Static | | | Rotating | | |
| --- | --- | --- | --- | --- | --- |
| Hybcell 1 | Hybcell 2 | Hybcell 3 | Hybcell 1 | Hybcell 2 | Hybcell 3 |
| 985 | 350 | 499 | 1072 | 487 | 1296 |
| 1035 | 384 | 602 | 1082 | 812 | 1497 |
| 1048 | 414 | 706 | 1182 | 1480 | 1502 |
| 1074 | 417 | 763 | 1378 | 1543 | 1529 |
| 1143 | 419 | 769 | 1426 | 1579 | 1591 |
| 1154 | 435 | 781 | 1504 | 1598 | 1650 |
| 1158 | 439 | 802 | 1554 | 1624 | 1719 |
| 1181 | 440 | 804 | 1555 | 1660 | 1779 |
| 1253 | 450 | 808 | 1610 | 1692 | 1804 |
| 1266 | 456 | 814 | 1610 | 1787 | 1822 |
| 1270 | 461 | 823 | 1621 | 1807 | 1865 |
| 1270 | 478 | 852 | 1640 | 1849 | 1890 |
| 1285 | 479 | 914 | 1662 | 1870 | 1927 |
| 1305 | 485 | 922 | 1818 | 1877 | 2096 |
| 1353 | 597 | 926 | | 1937 | 2111 |
| 1191 | 444 | 803 | 1522 | 1681 | 1734 |

| | Static incubation | Rotating incubation |
| --- | --- | --- |
| mean value intra | 813 | 1646 |
| standard dev. intra | 373 | 110 |
| ratio intra | 46% | 7% |

In this example, a test protocol is applied which serves for detection and quantification of morphine in the saliva by means of the inventive device:

1. Pre-treating the carriers (rotor with an Au/Pd coating)
   a. Washing in $NH_3/H_2O_2/H_2O$ at the ratio of 1:1:5 (5 min)
   b. Washing with $H_2O$
   c. Drying for 30 min at 50° C.
   d. Incubating with DSP in DMSO (1 mg/ml) for 30 min at room temperature
   e. Washing the carrier with acetone
   f. Drying for 30 min at 50° C.
2. Printing in $NaHCO_3$ buffer
3. Immobilising over night 4. Blocking with 0.5% Tween 20 in PBS
5. Incubating with saliva-containing solution (50%) and 1 ng/ml of morphine as well as 1 µl of labelled anti-morphine antibody (Dylight 547 cyanine-based dye)
6. Adding the saliva mixture to the inventive device (Rotor, Au/Pd-coated) and stirring for 5 min at 700 rpm
7. Washing with 0.5% Tween 20 in PBS three times
8. Detecting

EXAMPLE 2

Comparison of the Signal Level of Measurements with the Inventive Device in Case of Static and Rotating Incubation In this example, the effects of incubation time on the signal level were examined in case of static and rotating incubation. Experimentally, again, antibodies were tested in solution and antigen as regards the stationary phase (cf. Example 1). As can be seen from FIG. 33, the rotating incubation has a definite advantage over the static incubation in the course of time as regards the level of the individual measurements.

TABLE 2

Scanning settings were 0.9 7 300. The devices were labelled with 1 µl of antibody (1 mg/ml), incubated with Dylight 547 nm in a rotating or static manner. Evaluation was done with a diameter of 200 µm. The morphine-BSA signal was evaluated.

|  | Static incubation | | | | | Rotational incubation | | | | |
| --- | --- | --- | --- | --- | --- | --- | --- | --- | --- | --- |
|  | 1 min | 5 min | 15 min | 30 min | 90 min | 1 min | 5 min | 15 min | 30 min | 90 min |
|  | 63 | 73 | 579 | 771 | 1424 | 215 | 2019 | 3136 | 1865 | 2741 |
|  | 71 | 267 | 1000 | 850 | 2011 | 356 | 2037 | 3930 | 2071 | 3552 |
|  | 90 | 456 | 1274 | 858 | 2149 | 362 | 2048 | 4208 | 2147 | 4406 |
|  | 98 | 625 | 1437 | 1461 | 2360 | 370 | 2048 | 4262 | 2862 | 4463 |
|  | 120 | 650 | 1489 | 1659 | 2372 | 406 | 2117 | 4269 | 4166 | 4635 |
|  | 125 | 653 | 1870 | 2097 | 2426 | 430 | 2120 | 4271 | 4692 | 4643 |
|  | 133 | 660 | 1927 | 2704 | 2791 | 439 | 2186 | 4461 | 4947 | 4691 |
|  | 140 | 675 | 2142 | 2706 | 3426 | 459 | 2273 | 4472 | 5321 | 4840 |
|  | 152 | 678 | 2243 | 2824 | 3579 | 460 | 2313 | 4548 | 5324 | 5002 |
|  | 166 | 682 | 2261 | 3058 | 3757 | 472 | 2325 | 4552 | 5487 | 5177 |
|  | 190 | 686 | 2300 | 3093 | 4025 | 473 | 2335 | 4567 | 5884 | 5190 |
|  | 199 | 697 | 2465 | 3329 | 4199 | 479 | 2497 | 4603 | 5978 | 5270 |
|  | 263 | 711 | 2496 | 4106 | 4202 | 595 | 2599 | 5026 | 6704 | 6107 |
|  | 278 | 717 | 2807 | 4157 | 4357 | 597 | 2635 | 5158 | 7622 | 6621 |
|  | 281 | 834 | 2828 | 4402 | 5629 | 618 | 3238 | 5339 | 9044 | 9690 |
| Mean value | 152 | 652 | 1991 | 2536 | 3208 | 450 | 2260 | 4476 | 4865 | 4948 |
| Standard dev. | 50 | 69 | 427 | 935 | 803 | 63 | 179 | 233 | 1356 | 486 |
| Ratio | 33% | 11% | 21% | 37% | 25% | 14% | 8% | 5% | 28% | 10% |

EXAMPLE 3

Focussing Errors During Measurement of Samples in an Inventive Device

In order to test the significance of centric rotation (mounting) in the case of the inventive device, measurements of cylinder surfaces with labels were taken around the whole circumference. Measurement A=centric rotation occurred in the device described and used here. Measurement B=oscillating rotation occurred under the same conditions but without centred mounting with a device, wherein said device does have a rotor in a container but does not have means for centred positioning (cf. FIG. 36). Thus, an oscillation out of the optical focus could not be prevented. The boundaries at the labels were used as a degree for the sharpness of the illustration.

As shown in FIGS. 36A and B, it can be clearly seen that problems occur during measurements in the case of an uncentred mounting of the rotor in the sample container. The course of the focussing error across the cylinder jacket is illustrated in FIG. 37. Here, it becomes apparent that the illustration of the labels changes from sharp to unsharp, depending on the oscillation movement across the circumference. However, the centred mounting of the inventive device shows a constant sharpness with a small variation area (calculation tolerance).

EXAMPLE 4

Measurement of Bond Kinetics

In this example, it has been shown that a measurement over a period of time is rendered possible by the inventive device. Thus, the incubation and, consequently, the signal level is detectable as a function of the incubation time. This means a record of the bond kinetics under the conditions chosen without the need of interrupting the test.

FIG. 38 clearly shows a rise of the signal (means from 9 identical spots on the surface of the rotor of the inventive device) as a function of the incubation time. The test was done according to the protocol of example 1, wherein the measurements were done during incubation with the labelled antibody without removing the unbound antibody by washing. The equally increased background (labelled antibody present in the solution) was subtracted from the signal level. The remaining signal was included into the table as value. The signal value reached its maximum after 13 min. The test was ended.

Thus, not only bond kinetics or dissociation events (DNA-DNA hybridisations and/or dissociations and/or melting curves) may be established but also competitions (competitive and noncompetitive) may be measured.

The fluorescence-labelled antibody (1 µg/ml) served as a mobile phase, Spots:Antigen (1 mg/ml of spotting concentration morphine) served as a stationary phase. No washing was done between the scans. Incubation was effected at room temperature (20-24° C.).

The invention claimed is:

1. A device for the analysis of liquid samples, comprising a rotationally-symmetric rotor which is insertable into a sample container such that an annular gap is provided between the sample container and the rotor, where the rotor has at least one flow channel for transporting liquids and/or gases and where the rotor comprises a centered mount configured to be coupled to the sample container for centered mounting of the rotor relative to the sample container; and wherein the rotor is center-mounted via an elevation or dent oriented towards the interior of the sample container and located at the bottom of the sample container and a recess provided on the rotor which is complementary thereto.

2. The device of claim 1, further comprising at least one elevation on a jacket surface of the rotor or on an inner wall of the sample container.

3. The device of claim 1, further defined as adapted to provide torque to the rotor during use.

4. The device of claim 3, wherein the torque is provided to the rotor by a longitudinal body which extends axially to the rotor.

5. The device of claim 1, further comprising a lid for covering the sample container during use.

6. The device of claim 5, wherein the lid is detachable.

7. The device of claim 5, wherein the lid comprises a flow channel connected with the flow channel of the rotor.

8. The device of claim 7, wherein the flow channel of the lid has a smaller diameter than the flow channel of the rotor.

9. The device of claim 5, wherein the lid comprises a rim with a sealing lip.

10. The device of claim 5, wherein the lid fastens to the rotor.

11. The device of claim 10, wherein the lid fastens to the rotor via at least one radially-arranged elevation.

12. The device of claim 11, wherein the elevation comprises a spiral-shaped notch comprising a radial recess or a radial projection.

13. The device of claim 10, wherein the lid comprises a dent.

14. The device of claim 13, wherein the dent has a spiral-shaped notch, a radial projection or a radial recess.

15. The device of claim 5, further comprising at least one elevation on a jacket surface of the rotor or on an inner wall of the sample container.

16. The device of claim 15, wherein the lid is adapted to transfer torque to the rotor during use.

17. The device of claim 15, wherein the torque is transferred to the rotor during use via a longitudinal body which extends axially to the rotor.

18. The device of claim 1, wherein the elevation or dent and the recess have a cylindrical form, conical form, frustoconical form, or a combined form.

19. The device of claim 1, wherein the flow channel is connected with a center mount of the rotor.

20. The device of claim 19, wherein an inner side of the center mount of the rotor comprises at least one depression that extends along the mount and/or the flow channel.

21. The device of claim 1, wherein the dent is adapted to receive a cooling and/or heating device.

22. The device of claim 1, wherein the dent is adapted to transfer torque to the sample container during use.

23. The device of claim 22, further comprising a longitudinal body in the dent positioned axially to the rotor that transfers torque during use.

24. The device of claim 1, wherein the center mount comprises a magnetic bearing.

25. The device of claim 24, wherein at least one magnet is provided on the rotor.

26. The device of claim 25, wherein at least one magnet is provided on the sample container.

27. The device of claim 25, wherein the at least one magnet is a permanent magnet.

28. The device of claim 1, wherein the sample container is at least partially transparent.

29. The device of claim 1, wherein at least one flow channel of the rotor is arranged axially.

30. The device of claim 1, wherein a diameter of the flow channel of the rotor is larger in a bottom region of the sample container than in an opening region of the sample container.

31. The device of claim 1, wherein the rotor and/or an inner side of the sample container comprises at least one binding partner for binding at least one ligand during use.

32. The device of claim 31, wherein the at least one binding partner is a biomolecule.

33. The device of claim 32, wherein the biomolecule is an antibody, an antigen or a nucleic acid.

34. The device of claim 1, wherein the rotor comprises at least one radial outward-oriented projection as a spacing element, and/or the inner jacket of the sample container comprises at least one radial inward-oriented projection as a spacing element.

35. The device of claim 34, wherein the sample container is adapted for radial fixation in a cartridge during use.

36. The device of claim 35, wherein the sample container comprises at least one projection on a bottom portion that is adapted for radial fixation of the cartridge.

37. The device of claim 36, wherein the projection is a nodule.

38. The device of claim 1, wherein the rotor and/or the sample container and/or the lid is made of plastic.

39. The device of claim 38, wherein the plastic is a cyclo-olefin copolymer, polystyrene, polypropylene, polyethylene, acetate polymer, acrylnitrile butadiene stryrene, polymethyl metacrylate, PVC, polyethylene terephptalate, polytetrafluoroethylene, or a combination thereof.

40. The device of claim 1, wherein the surface of the rotor is coated with a metal, silicon, silicon compound with carbon, or a combination thereof.

41. The device of claim 40, wherein the surface of the rotor is coated with a semiconductor metal.

42. The device of claim 40, wherein the surface of the rotor is coated with a silicon compounded with graphite, DLC, and/or diamond.

43. The device of claim 40, wherein the surface of the rotor is coated with silicon oxide.

44. The device of claim 40, wherein the metal is gold, palladium, silver, or a combination thereof.

45. The device of claim 1, further defined as a flow-through cell.

46. A cartridge adapted to receive a device of claim 1, comprising an opening for introducing the sample container and a lateral delimitation provided with a recess, wherein the recess is designed for axial fixing of the rotor.

47. The cartridge of claim 46, wherein a delimitation of the cartridge comprises a depression for receiving the cartridge during use and the depression faces a lateral delimitation comprising a recess.

48. A rotor for use with a sample container for the analysis of liquid samples, comprising:
a rotationally-symmetric rotor configured to be insertable into a sample container such that an annular gap is provided between the sample container and the rotor;

where the rotor has at least one flow channel for transporting liquids and/or gases into and/or from the interior of the sample container during use; and where the rotor comprises a centered mount configured to be coupled to the sample container for centered mounting of the rotor relative to the sample container; and wherein the rotor is center-mounted via an elevation or dent oriented towards the interior of the sample container and located at the bottom of the sample container and a recess provided on the rotor which is complementary thereto.

49. A sample container in combination with a rotationally-symmetric rotor having a centered mount and at least one flow channel, such that the sample container and rotor can be coupled for the analysis of liquid samples, the sample container comprising:

a sample container configured to receive the rotor that such that an annular gap is provided between the sample container and the rotor, and the at least one flow channel can transport liquids and/or gases into and/or from the interior of the sample container during use;

where the sample container is configured to be coupled to the centered mount of the rotor for centered mounting of the rotor relative to the sample container; and wherein the rotor is center-mounted via an elevation or dent oriented towards the interior of the sample container and located at the bottom of the sample container and a recess provided on the rotor which is complementary thereto.

50. A method comprising obtaining a device of claim 1 and using the device to detect a substance in a sample, conduct an enzymatic reaction, and/or amplify a nucleic acids.

51. The method of claim 50, further defined as comprising qualitative and/or quantitative detection of substances in a body fluid.

52. The method of claim 51, wherein the body fluid is blood or saliva.

* * * * *

UNITED STATES PATENT AND TRADEMARK OFFICE
CERTIFICATE OF CORRECTION

PATENT NO. : 7,927,546 B2
APPLICATION NO. : 12/089358
DATED : April 19, 2011
INVENTOR(S) : Bernhard Ronacher et al.

It is certified that error appears in the above-identified patent and that said Letters Patent is hereby corrected as shown below:

Column 25, line 6, after "gases" insert --into and/or from the interior of the sample container during use,--.

Signed and Sealed this
Fifth Day of July, 2011

David J. Kappos
*Director of the United States Patent and Trademark Office*